Figure 1:
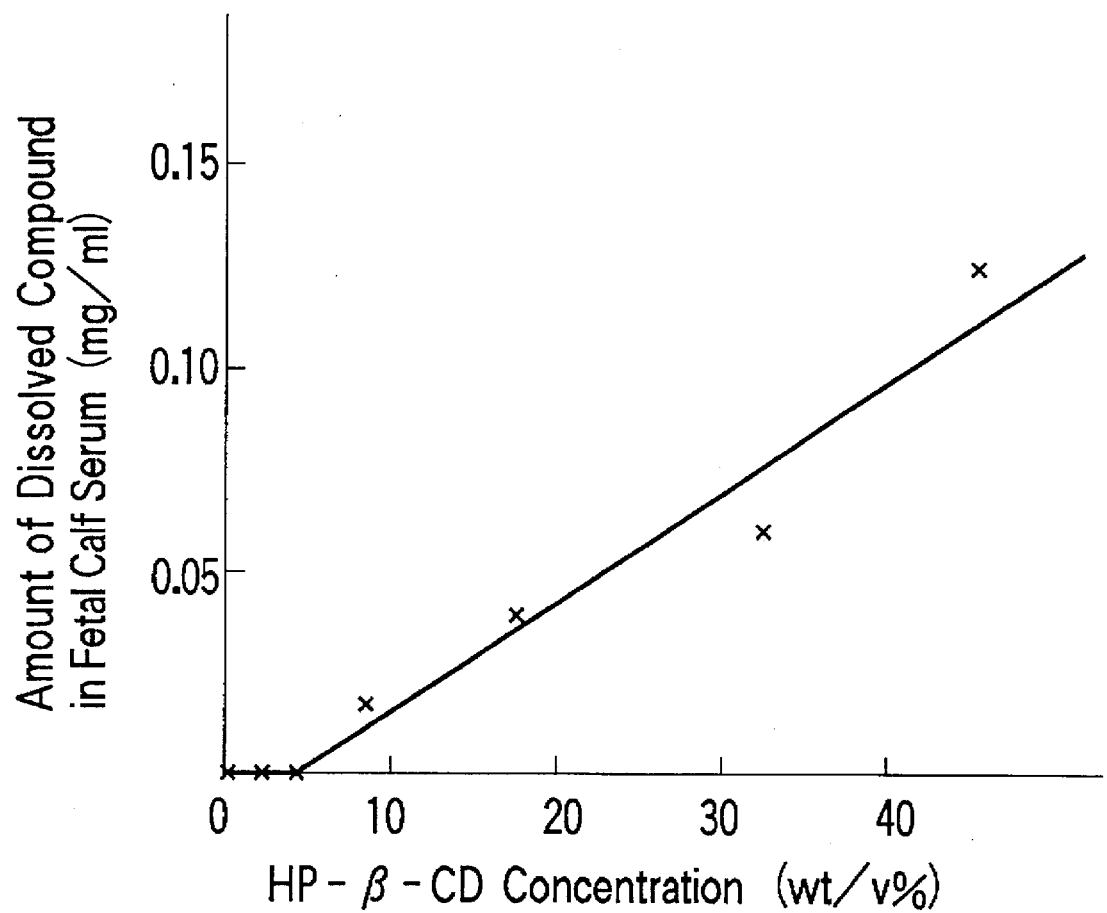

United States Patent [19]

Chen et al.

[11] Patent Number: 5,670,530

[45] Date of Patent: Sep. 23, 1997

[54] ANTI-CANCER COMPOSITION COMPRISING RHODACYANINE COMPOUND AND CYCLODEXTRIN

[75] Inventors: Lan Bo Chen, Lexington, Mass.; Tadao Shishido, Kanagawa-ken, Japan

[73] Assignees: Fuji Photo Film Co., Ltd., Kanagawa, Japan; Dana Farber Cancer Institute, Boston, Mass.

[21] Appl. No.: 474,974

[22] Filed: Jun. 7, 1995

Related U.S. Application Data

[63] Continuation of Ser. No. 966,422, Oct. 26, 1992, abandoned.

[51] Int. Cl.$^6$ ................................... A61K 31/425
[52] U.S. Cl. .................. 514/366; 514/58; 514/314; 514/338; 514/367; 514/369; 514/375; 514/376; 514/443
[58] Field of Search .................. 514/58, 443, 314, 514/338, 366, 367, 369, 375, 376

[56] References Cited

U.S. PATENT DOCUMENTS 4,727,064  2/1988  Pitha ............................... 514/58

FOREIGN PATENT DOCUMENTS

WO8502767  7/1985  WIPO .......................... 514/58

*Primary Examiner*—Richard L. Raymond
*Attorney, Agent, or Firm*—Sughrue, Mion, Zinn, Macpeak, and Seas.

[57] ABSTRACT

An anti-cancer composition comprising a rhodacyanine compound and cyclodextrin or derivative thereof, wherein said rhodacyanine compound is selected from the group consisting of compounds represented by the following Formula (I), the cation moiety of which has a log P value of 4.5–12:

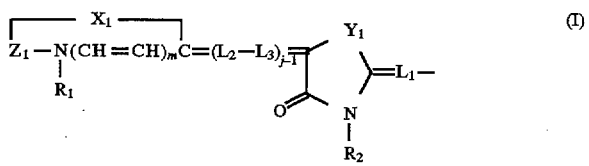

(I)

-continued

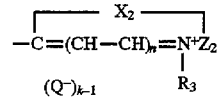

wherein $X_1$ and $X_2$, which may be the same or different, each represents O, S, Se,

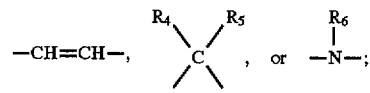

$Y_1$ represents O, S, Se, or

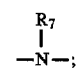

$R_1$ and $R_3$, which may be the same or different, each represents an alkyl group;

$R_2$ represents an alkyl group, an aryl group or a heterocyclic group;

$Z_1$ and $Z_2$, which may be the same or different, each represents an atomic group necessary to form a 5- or 6-membered ring;

$L_1$, $L_2$ and $L_3$, which may be the same or different, each represents a methine group or nitrogen atom and $L_1$ and $R_3$ may combine and form a 5- or 6-membered ring;

$R_4$ and $R_5$, which may be the same or different, each represents an alkyl group;

$R_6$ and $R_7$, which may be the same or different, each represents an alkyl group or an aryl group;

Q represents a pharmaceutically acceptable anion;

j and k, which may be the same or different, each represents 1 or 2;

m and n, which may be the same or different, each represents 0 or 1.

19 Claims, 3 Drawing Sheets

ANTI-CANCER COMPOSITION COMPRISING RHODACYANINE COMPOUND AND CYCLODEXTRIN

This is a continuation of application Ser. No. 07,966,422 filed Oct. 26, 1992 (abandoned).

FIELD OF THE INVENTION

This invention relates to an anti-cancer composition comprising a rhodacyanine compound and a cyclodextrin or derivative thereof and a method for treatment of cancer using the composition. More particularly, this invention relates to an anti-cancer composition comprising a hardly-water-soluble rhodacyanine compound effective as an anti-tumor agent, the solubility of which is improved by a cyclodextrin or derivative thereof.

BACKGROUND OF THE INVENTION

It has been demonstrated that certain compounds referred to as rhodacyanine show an excellent anti-tumor effect in vitro and in vivo tests using animal, as disclosed in U.S. patent application Ser. No. 692,347 filed on Apr. 26, 1991, now abandoned, and U.S. patent application Ser. No. 744,130 filed on Aug. 13, 1991, now abandoned. Therefore, the rhodacyanine compounds are considered to be available for anti-tumor agents by themselves. However, among these, some rhodacyanine compounds are hardly soluble in solvents, especially in water, and, as a result, it causes a problem in that the compounds precipitate in the body after administering solutions of the compounds, in particular, by intravenous injection. For example, if the compounds precipitate in blood after intravenous injection, the precipitate may form a thrombus in the lungs, and then obstruct the blood circulation, which may result in a symptom such as respiratory insufficiency. If the compounds also precipitate after subcutaneously administration, the precipitate may cause inflamation at the administration site. On the other hand, if the compounds precipitate after intraperitoneally administration, the precipitate may cause formation of abdominal dropsy, which may result in a peritonitis.

Hitherto, it has been known that various surface active agents are employed as a solubilizer to improve solubility of a compound being hardly soluble in water. The solubilizer which is conventionally used in injection could improve water-solubilities of the hardly-water-soluble rhodacyanine compounds, but the improvement was not sufficient. Further, it was found that the solubilizer scarcely improves their solubility in human serum. Accordingly, the problem mentioned above, i.e., precipitation after intravenous injection of an anti-cancer composition comprising a hardly-soluble rhodacyanine compound can not be solved by using such a solubilizer.

Unlike the foregoing manner, Japanese Un-examined Patent Publication (Jr Kokai) No. Hei 4-4259 discloses that an organic carboxylate anion group is introduced into an anion moiety of a rhodacyanine compound to improve water-solubility of the rhodacyanine compound. However, it has been found that even through the water-solubility of the rhodacyanine compound is improved by this manner, the resulting rhodacyanine compound sometimes reprecipitates in blood after intravenous injection of an aqueous solution of the compound.

Accordingly, it is desired to provide an anti-cancer composition containing the hardly-water-soluble rhodacyanine compound in the form of a solution in which the compound does not precipitate in blood or other body fluid after administration.

On the other hand, U.S. Pat. No. 4,727,064 and International Patent application No. WO-8,502,767 disclose that cyclodextrins are utilized for stabilization or solubilization of a drug which is unstable or hardly soluble in water. The mechanism of the stabilization or solubilization is assumed to be a clathration of the drug (substrate) into a hollow part of the cyclodextrin (acceptor).

However, there are various factors between the substrate and the acceptor which seriously affect the clathration, for example, steric factors, electrostatic factors and the like. From this, it appears that the acceptor is specific to the substrate for the clathration. Therefore, it is very difficult to expect that cyclodextrin would improve solubility of a specific compound.

SUMMARY OF THE INVENTION

Accordingly, a primary object of this invention is to provide an anti-cancer composition containing the hardly-water-soluble rhodacyanine compound in the form of a solution, which makes it possible to improve the solubility of the rhodacyanine compound.

An another object of this invention is to provide an anti-cancer composition which does not precipitate in blood or other body fluid after administration.

An another object of this invention is to provide a method for treatment of cancer comprising administering the anti-cancer composition described above to a mammalian host in need of such treatment.

These and other objects of this invention will be apparent from the following description and Examples.

As a result of extensive research, it has been found that cyclodextrins and derivatives thereof can improve water-solubility of the rhodacyanine compound and, as a result, they can prevent precipitation of the compound in blood after intravenously injection of an aqueous solution of the rhodacyanine compound.

In one embodiment, the present invention provides an anti-cancer composition comprising a rhodacyanine compound and a cyclodextrin or derivative thereof, said rhodacyanine compound being selected from the group consisting of compounds represented by the following Formula (I) and the cation moiety of which has a log P value of 4.5–12.

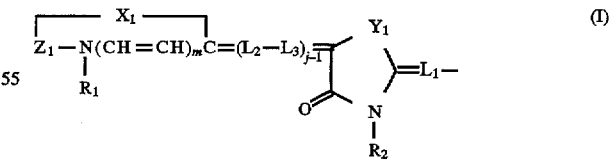

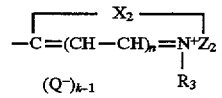

wherein $X_1$ and $X_2$, which may be the same or different, each represents O, S, Se,

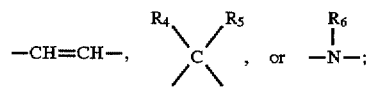

$Y_1$ represents O, S, Se, or

$R_1$ and $R_3$, which may be the same or different, each represents an alkyl group;

$R_2$ represents an alkyl group, an aryl group or a heterocyclic group;

$Z_1$ and $Z_2$, which may be the same or different, each represents an atomic group necessary to form a 5- or 6-membered ring;

$L_1$, $L_2$ and $L_3$, which may be the same or different, each represents a methine group or nitrogen atom and $L_1$ and $R_3$ may combine and form a 5- or 6-membered ring;

$R_4$ and $R_5$, which may be the same or different, each represents an alkyl group;

$R_6$ and $R_7$, which may be the same or different, each represents an alkyl group or an aryl group;

Q represents a pharmaceutically acceptable anion;

j and k, which may be the same or different, each represents 1 or 2;

m and n, which may be the same or different, each represents 0 or 1.

In another embodiment, the present invention provides a method for treatment of cancer comprising administering the anti-cancer composition to a mammalian host in need of such treatment.

BRIEF DESCRIPTION OF THE ACCOMPANYING DRAWINGS

Figure 2:
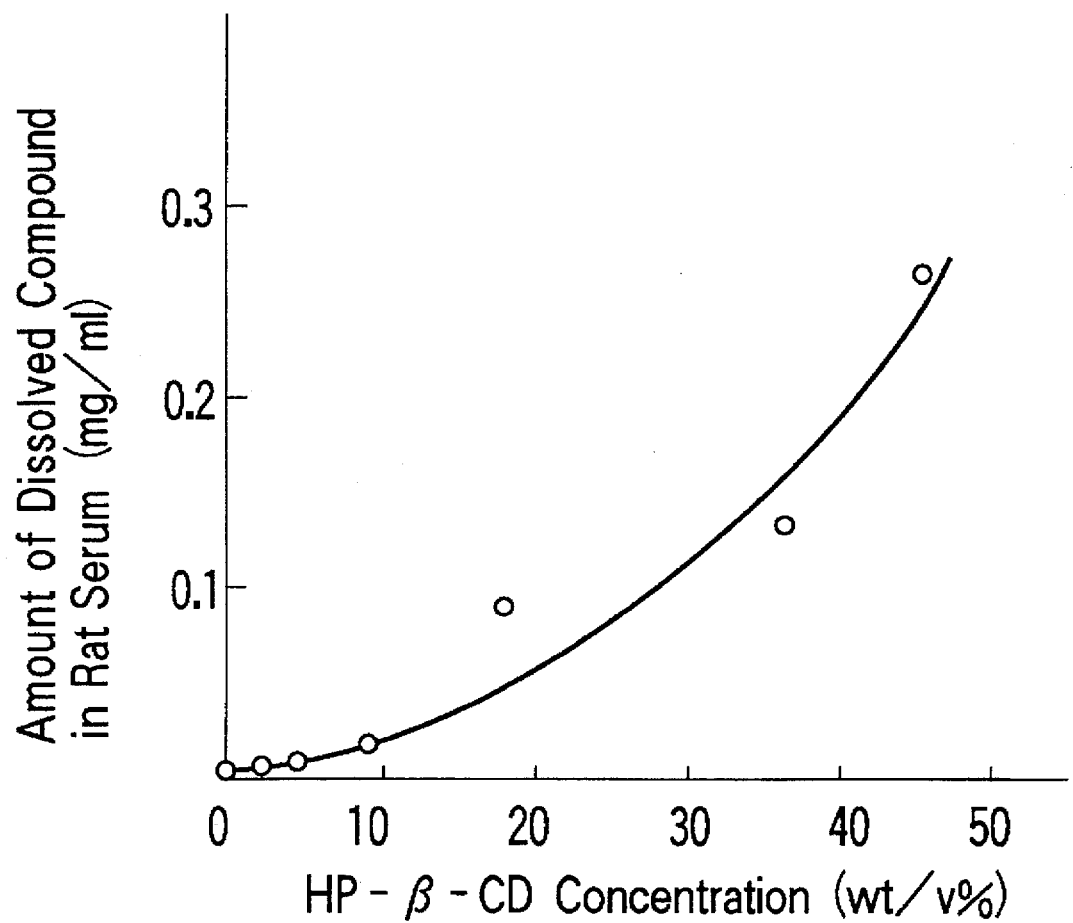
Figure 3:
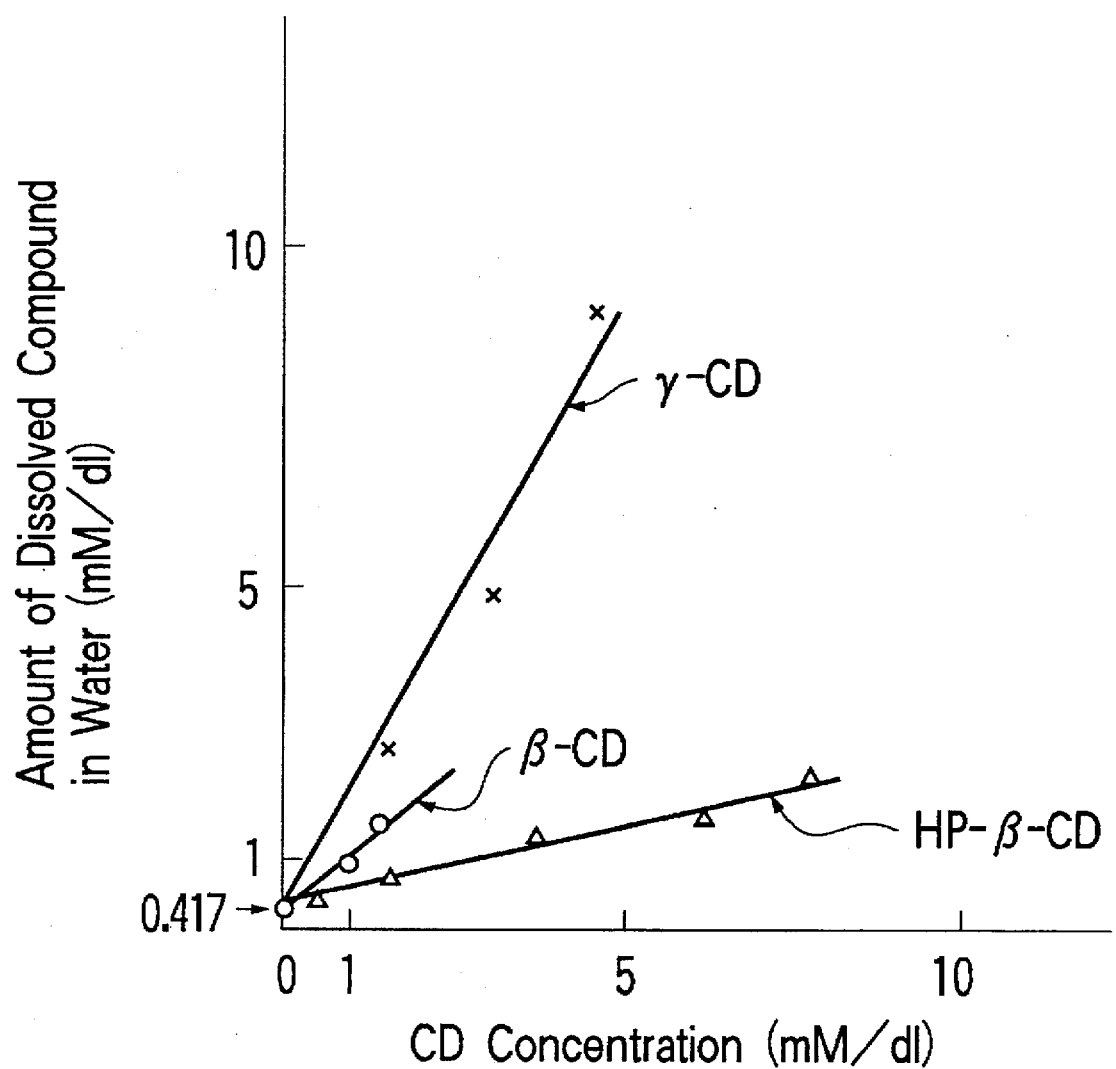

FIGS. 1 to 3 are graphical presentations of the results obtained in the Examples described hereinafter.

DESCRIPTION OF THE PREFERRED EMBODYMENTS

Preferred embodiments of this invention include the composition and method as described above where the rhodacyanine compound is selected from the group consisting of compounds represented by the above Formula (I) and the cation moiety of which has a log P value of 5–11.

In further preferred embodiments of this invention, the rhodacyanine compound is selected from the group consisting of the compounds of the following Formulae (II) to (V) set forth below:

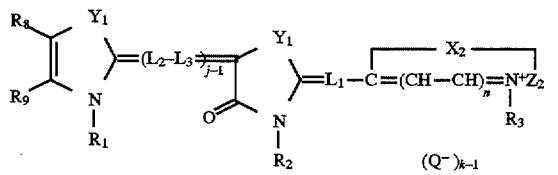

wherein $Z_2$, $Y_1$, $X_1$, $X_2$, $R_1$, $R_2$, $R_3$, $L_1$, $L_2$, $L_3$, Q, j, k and n all have the same meanings as defined above;

$R_8$ and $R_9$, which may be the same or different, each represents a hydrogen atom, an alkyl group or an aryl group, or $R_8$ and $R_9$ may combine and form a fused 5- or 6-membered ring;

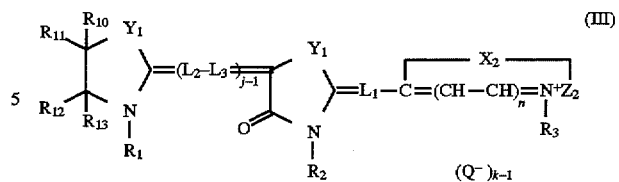

wherein $X_1$, $Y_1$, $X_2$, $Z_2$, $R_1$, $R_2$, $R_3$, Q, j, k, $L_1$, $L_2$, $L_3$ and n have the same meanings as defined above;

$R_{10}$, $R_{11}$, $R_{12}$ and $R_{13}$, which may be the same or different, each represents a hydrogen atom, an alkyl group or an aryl group, or any two of $R_{10}$ to $R_{13}$ may combine and form a 5- or 6-membered ring;

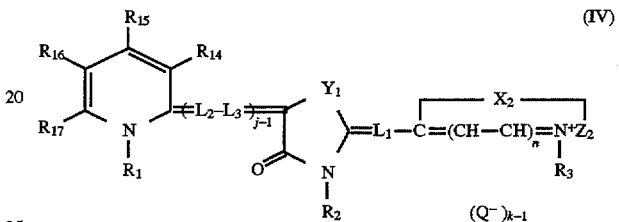

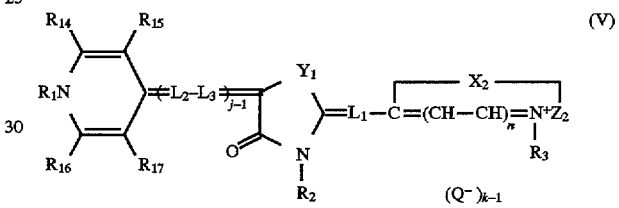

wherein $Y_1$, $X_2$, $Z_2$, $R_1$, $R_2$, $R_3$, Q, j, k, $L_1$, $L_2$, $L_3$ and n have the same meanings as define above;

$R_{14}$, $R_{15}$, $R_{16}$, and $R_{17}$, which may be the same or different, each represents a hydrogen atom, an alkyl group, an aryl group, an alkoxy group, an aryloxy group, an acyl group, an alkoxycarbonyl group, a benzoyl group, an ureido group, an amino group, an amido group, an sulfamido group, a carbomoyl group, a sulfamoyl group, a halogen atom, a nitro group, a cyano group, a hydroxy group or a carboxyl group, or any adjacent two of $R_{14}$ to $R_{17}$ may combine and form a 5- or 6-membered ring.

Furthermore preferred embodiments of this invention include composition and method as described above where the composition is a composition for injection.

log P value is often utilized as a measure for estimating solubility of an organic compound in water (or in an organic solvent). The log P value indicates a distribution ratio of a compound between water phase and n-octanol phase, and it can be determined for each compound by measurement or calculation.

Then, the inventors of the present invention determined the log P value for the cation moiety of several rhodacyanine compounds by calculation using the PROLOGP (ver 4.1) method developed by Compu Drug Corporation and also measured solubility of the rhodacyanine compounds in human serum at 37° C. in order to estimate the degree of precipitation of the compounds in blood.

TABLE A shows the log P values for the cation moiety of each rhodacyanine compound which were obtained by calculation using the PROLOGP method and experimental data which were obtained by measuring the amounts (mg/ml, at 37° C.) of rhodacyanine compound dissolved in human serum.

TABLE A

| Compound | logP | solubility in human serum 37° C., mg/ml |
|---|---|---|
| (structure) | 2.89 | >1 |
| (structure) | 3.85 | >1 |
| (structure) | 4.29 | >1 |
| (structure) | 4.38 | 0.3 |
| (structure) | 4.68 | <1 |
| (structure) | 4.69 | <1 |
| (structure) | 5.05 | <0.1 |
| (structure) | 5.42 | <0.1 |

TABLE A-continued

| Compound | logP | solubility in human serum 37° C., mg/ml |
|---|---|---|
|  | 5.95 | <0.1 |
|  | 6.70 | <0.1 |
|  | 7.15 | <0.1 |
|  | 8.89 | <0.1 |

From the results set forth in TABLE A, it is clear that the solubility of the rhodacyanine compounds in human serum at 37° C. is 0.1 mg/ml or lower when the log P values of the cation moiety of the rhodacyanine compound are not less than 4.5, especially not less than 5. This indicates that a high possibility in that the rhodacyanine compound, the cation moiety of which has a log P value of not less than 4.5, especially not less than 5, would precipitate in blood after injecting a solution of the compound in high amount of dose into a body.

Therefore, the foregoing problem will be solved by improving the solubility in body fluid, in particular blood, of the rhodacyanine compounds, the cation moiety of which has a log P value of 4.5–12, especially 5–11.

In greater detail, in the Formulae (I) to (V)

$X_1$ and $X_2$, individually, represents an oxygen atom, a sulfur atom, a selenium atom,

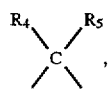

—CH=CH— or a group of the formula

where $R_4$ and $R_5$ each represents an alkyl, i.e., an unsubstituted or substituted alkyl group such as a straight-chain, branched chain or cyclic alkyl group, and $R_6$ is an alkyl, i.e., an unsubstituted or substituted alkyl group such as a straight-chain, branched chain or cyclic alkyl group, an aryl, i.e. an unsubstituted or substituted aryl group such as a monocyclic or bicyclic aryl group, or a heterocyclic, i.e., an unsubstituted or substituted heterocyclic group such as a 5- to 6-membered heterocyclic group which tan be saturated or unsaturated and can contain one or more nitrogen atoms, oxygen atoms and sulfur atoms.

$Y_1$ represents an oxygen atom, a sulfur atom, a selenium atom or a group of the formula

where $R_7$ is an alkyl, i.e., an unsubstituted or substituted alkyl group such as a straight-chain, branched chain or cyclic alkyl group, an aryl, i.e., an unsubstituted or substituted aryl group such as a monocyclic or bicyclic aryl group, or a heterocyclic group, i.e., an unsubstituted or substituted heterocyclic group such as a 5- to 6-membered heterocyclic group which can be saturated or unsaturated and can contain one or more nitrogen atoms, oxygen atoms and sulfur atoms.

$R_1$, $R_2$ and $R_3$ each individually represents an alkyl, i.e., an unsubstituted or substituted alkyl group such as a straight-chain, branched chain or cyclic alkyl group and $R_2$ can additionally be an aryl, i.e., an unsubstituted or substituted aryl group such as a monocyclic, bicyclic or tricyclic aryl group or a heterocyclic, i.e., an unsubstituted or substituted heterocyclic group such as a 5- to 6-membered heterocyclic group which can be saturated or unsaturated and can contain one or more nitrogen atoms, oxygen atoms and sulfur atoms as hetero atoms.

$Z_1$ and $Z_2$, which may be the same or different, each represents an atomic group necessary to form a saturated or unsaturated 5- or 6-membered ring which may contain one or more nitrogen atoms, oxygen atoms, sulfur atoms or selenium atoms as hetero atoms and $Z_1$ and $Z_2$ may be each substituted or condensed with another ring such as a saturated or unsaturated ring.

$L_1$, $L_2$ and $L_3$ each represents a methine group, i.e., an unsubstituted or substituted methine group or nitrogen atom and when $L_1$ is a substituted methine group, $L_1$ and $R_3$ may combine to form a saturated or unsaturated 5- or 6-membered ring.

$R_8$ and $R_9$ each represents a hydrogen atom or an alkyl, i.e., an unsubstituted or substituted alkyl group such as a straight-chain, branched chain or cyclic alkyl group and moreover, $R_8$ and $R_9$ represents an aryl, i.e., an unsubstituted or substituted aryl group such as a monocyclic, bicyclic or tricyclic aryl group or $R_8$ and $R_9$ may combine and form a saturated or unsaturated fused 5- or 6-membered ring which may be substituted.

$R_{10}$, $R_{11}$, $R_{12}$ and $R_{13}$ each represents a hydrogen atom or an alkyl, i.e. an unsubstituted or substituted alkyl group such as a straight-chain, branched chain or cyclic alkyl group and moreover, $R_{10}$, $R_{11}$, $R_{12}$ and $R_{13}$ represents an aryl, i.e., an unsubstituted or substituted aryl group such as a monocyclic, bicyclic or tricyclic aryl group.

Further, any two of $R_{10}$, $R_{11}$, $R_{12}$ and $R_{13}$ may combine and form an unsubstituted or substituted 5- or 6-membered ring. Preferred are carbocyclic rings.

$R_{14}$, $R_{15}$, $R_{16}$ and $R_{17}$ each represents a hydrogen atom or an alkyl group, i.e., an unsubstituted or substituted alkyl group such as a straight-chain, branched chain or cyclic alkyl group and moreover, $R_{14}$, $R_{15}$, $R_{16}$ and $R_{17}$ each represents an aryl, i.e., an unsubstituted or substituted aryl group such as a monocyclic or bicyclic aryl group.

Further, $R_{14}$, $R_{15}$, $R_{16}$ and $R_{17}$ each represents an unsubstituted or substituted alkoxy group, for example, an alkoxyl group where the alkyl moiety thereof is a straight-chain or branched chain alkyl moiety; an unsubstituted or substituted aryloxy group, for example, an aryloxy group where the aryl moiety thereof is monocyclic or bicyclic; an unsubstituted or substituted acyl group, for example, an alkylacyl group where the alkyl moiety thereof is a straight-chain or branched chain alkyl moiety or an arylacyl group where the aryl moiety thereof is monocyclic or bicyclic; an unsubstituted or substituted alkoxycarbonyl group, for example, an alkoxycarbonyl group where the alkyl moiety thereof is a straight-chain or branched chain alkyl moiety; an unsubstituted or substituted benzoyl group; an unsubstituted or substituted ureido group, for example, an alkylureido group where the alkyl moiety thereof is a straight-chain or branched chain alkyl moiety or an arylureido group where the aryl moiety thereof is monocyclic or bicyclic; an unsubstituted or substituted amino group, for example, a mono- or di-alkylamino group where the alkyl moiety thereof is a straight-chain or branched chain alkyl moiety or a mono- or di-arylamino group where the aryl moiety thereof is a monocyclic or bicyclic; an unsubstituted or substituted amido group, for example, a mono- or di-alkylamido group where the alkyl moiety thereof is a straight-chain or branched chain alkyl moiety or a mono- or di- arylamido group where the aryl moiety thereof is monocyclic or bicyclic; an unsubstituted or substituted sulfamido group, for example, an alkylsulfamido group where the alkyl moiety thereof is a straight chain or branched chain alkyl moiety or an arylsulfamido group where the aryl moiety thereof is monocyclic or bicyclic; an unsubstituted or substituted carbamyl group, for example, an alkylcarbamyl group where the alkyl moiety thereof is a straight chain or branched chain alkyl moiety or an arylcarbamyl group where the aryl moiety thereof is monocyclic or bicyclic; an unsubstituted or substituted sulfamoyl group, for example, an alkylsulfamoyl group where the alkyl moiety thereof is a straight chain or branched chain alkyl moiety or an arylsulfamoyl group where the aryl moiety therof is monocyclic or bicyclic; a halogen atom such as a bromine atom, a chlorine atom, an iodine atom or a fluorine atom; a nitro group; a cyano group; a hydroxy group; or a carboxy group, or any adjacent two of $R_{14}$ to $R_{17}$ may combine and form a saturated or unsaturated 5- or 6-membered ring which may have other rings fused therewith.

Q represents a pharmaceutically acceptable anion necessary for electrical charge balance, j and k each is 1 or 2 and m and n each is 0 or 1.

More specifically, as described above, $R_1$ and $R_3$ individually can represent an alkyl group which may be unsubstituted or substituted. Suitable examples of alkyl groups include straight-chain, branched chain and cyclic alkyl groups having 1 to 15 carbon atoms, more preferably 1 to 10 carton atoms, even more preferably 1 to 8 carbon atoms.

Specific examples of alkyl groups for $R_1$ and $R_3$ include methyl, ethyl, n-propyl, i-propyl, n-butyl, i-butyl, sec-butyl, tert-butyl, n-pentyl, hexyl, heptyl, octyl, cyclopropyl, cyclopentyl, cyclohexyl, 2-propenyl, 2-butenyl, 3-hexenyl and the like. Specific examples of suitable substituents which can be present on the alkyl group when $R_1$ and $R_3$ represent a substituted alkyl group include halogen atoms such as chlorine, bromine, fluorine and iodine, an aryl group, an alkoxy group, a hydroxy group, and the like. A preferred number of carbon atoms for the unsubstituted and substituted alkyl groups for $R_1$ and $R_3$ ranges from 1 to 15, more preferably 1 to 10, most preferably 1 to 8. Specific examples of alkyl groups substituted by halogen atoms include trifluoromethyl, trifluoroethyl, tetrafluoropropy and pentafluoropropyl group.

As defined above, $R_2$, $R_6$ and $R_7$ represents an alkyl group which can be a straight-chain, branched chain or cyclic alkyl group and which may be substituted. Suitable examples of alkyl groups and substituents thereon are as described above for $R_1$ and $R_3$. A preferred number of carbon atoms for the alkyl group represented by $R_2$, $R_6$ and $R_7$ is from 1 to 15 carbon atoms, more preferably 1 to 10 carbon atoms, most preferable is 1 to 8 carbon atoms.

The aryl group represented by $R_2$, $R_6$ and $R_7$ above can be a monocyclic, bicyclic or tricyclic aryl group such as a phenyl group, a biphenyl group, a naphthyl group or an anthracenyl group and such may be unsubstituted or substituted. Suitable examples of substituents which can be present on the aryl group represented by $R_2$, $R_6$ and $R_7$ include one or more of a halogen atom such as chlorine, bromine, fluorine or iodine, an alkyl group, an alkoxy group, a hydroxy group, a nitro group, a cyano group, an amino group, an alkyl- or aryl-substituted amino group, an acylamino group, a sulfonylamino group, a carbamoyl group, a sulfamoyl group, a carboxyl group, an alkoxycarbonyl group, and the like. A suitable number of carbon atoms for the aryl group for $R_2$, $R_6$ and $R_7$ is 6 to 20, preferably 6 to 15, more preferably 6 to 8.

The heterocyclic ring represented by $R_2$, $R_6$ and $R_7$ can be a 5- to 6-membered heterocyclic ring containing one or more oxygen atoms, sulfur atoms or nitrogen atoms as hereto atoms. Suitable examples of heterocyclic rings represented by $R_2$, $R_6$ and $R_7$ include an imidazole ring, a thiazole ring, a pyrrole ring, a pyrazole ring, a furan ring, a thiophene ring, a piperidine ring, a morpholine ring, a piperadine ring, a pyrazine ring, a pyridine ring, a pyrimidine ring, and the like. These heterocyclic rings may be substituted, for example, by substituents as described above for the aryl group for $R_2$, $R_6$ and $R_7$ or may be condensed with another ring such as a saturated or unsaturated ring.

Examples of alkyl groups represented by $R_4$ and $R_5$ include unsubstituted or substitutred alkyl groups having from 1 to 15 carbon atoms, more preferably 1 to 10 carbon atoms. Suitable examples of suitable alkyl groups include those described above for $R_1$ and $R_3$ and substituents which can be present on the alkyl group represented by $R_4$ and $R_5$ include an alkyl group, an alkoxy group, a hydroxy group, a cyano group, a halogen atom, and the like.

Examples of alkyl groups represented by $R_6$ and $R_7$ above include alkyl groups as described above for $R_4$ and $R_5$. A suitable number of carbon atoms for the alkyl group for $R_6$ and $R_7$ is 1 to 15 carbon atoms, more preferably 1 to 10 carbon atoms. Further, $R_6$ and $R_7$ represents an unsubstituted or substituted aryl group which includes monocyclic, bicyclic and tricyclic aryl groups. A suitable number of carbon atoms for the aryl group for $R_6$ and $R_7$ is 6 to 20 carbon atoms, more preferably 6 to 15 carbon atoms. Specific examples of suitable aryl groups for $R_6$ and $R_7$ and substituents therefore include those described above for $R_2$.

The alkyl group represented by $R_8$, $R_9$, $R_{10}$, $R_{11}$, $R_{12}$, $R_{13}$, $R_{14}$, $R_{15}$, $R_{16}$ and $R_{17}$ above can be straight-chain, branched chain or cyclic and can include 1 to 15 carbon atoms, more preferably 1 to 10 carbon atoms, even more preferably 1 to 8 carbon atoms. The alkyl group represented by $R_8$, $R_9$, $R_{10}$, $R_{11}$, $R_{12}$, $R_{13}$, $R_{14}$, $R_{15}$, $R_{16}$ and $R_{17}$ can also be a unsubstituted alkyl group. Specific examples of alkyl group for $R_8$, $R_9$, $R_{10}$, $R_{11}$, $R_{12}$, $R_{13}$, $R_{14}$, $R_{15}$, $R_{16}$ and $R_{17}$ include methyl, ethyl, n-propyl, i-propyl, 2-propenyl, n-butyl, i-butyl, sec-butyl, tert-butyl, n-pentyl, hexyl, heptyl, octyl, cyclopropyl, cyclopentyl, cyclohexyl and the like. Specific examples of suitable substituents which can be present on the alkyl group when $R_8$, $R_9$, $R_{10}$, $R_{11}$, $R_{12}$, $R_{13}$, $R_{14}$, $R_{15}$, $R_{16}$ and $R_{17}$ represent a substituted alkyl group include halogen atoms such as chlorine, bromine, fluorine and iodine, an aryl group, an alkoxy group, a hydroxy group, ahd the like. A preferred number of carbon atoms for the unsubstituted and substituted alkyl groups for $R_8$, $R_9$, $R_{10}$, $R_{11}$, $R_{12}$, $R_{13}$, $R_{14}$, $R_{15}$, $R_{16}$ and $R_{17}$ ranges from 1 to 15, more preferably 1 to 10.

The aryl group represented by $R_8$, $R_9$, $R_{10}$, $R_{11}$, $R_{12}$, $R_{13}$, $R_{14}$, $R_{15}$, $R_{16}$ and $R_{17}$ can be a monocyclic, bicyclic or tricyclic aryl group such as a phenyl group, a biphenyl group, a naphthyl group or an anthracenyl group and such may be unsubstituted or substituted. Suitable examples of substituents which can be present on the aryl group represented by $R_8$–$R_{17}$ include one or more of a halogen atom such as chlorine, bromine, fluorine or iodine, an alkyl group, an alkoxy group, a hydroxy group, a nitro group, a cyano group, an amino group, an alkyl- or aryl-substituted amino group, an acylamino group, a sulfonylamino group, a carbamoyl group, a sulfamoyl group, a carboxyl group, an alkoxycarbonyl group, and the like. A suitable number of carbon atoms for the aryl group for $R_8$ to $R_{17}$ is 6 to 20, preferably 6 to 15.

Examples of the rings formed by binding $R_8$ with $R_9$ includes a benzene ring, naphthalene ring, dihydronaphthalene ring, anthracene ring, and phenanthrene ring. Suitable examples of substituents which can further be present on the rings formed by binding $R_8$ with $R_9$ include halogen atoms, a hydroxy group, an alkyl group preferably having 1 to 5 carbon atoms, an aryl group preferably having 6 to 8 carbon atoms, an alkoxy group preferably having 1 to 5 carbon atoms, an aryloxy group preferably having 6 to 8 carbon atoms, an alkoxycarbonyl group preferably having 2 to 6 carbon atoms and acyloxy group preferably having 2 to 6 carbon atoms. More preferable substituents are one or more chlorine atoms, one or more fluorine atoms, a methoxy group, an ethoxy group, a trifluoromethyl group, a methoxycarbonyl group, a phenyl group and a methylenedioxy group.

Moreover, two of $R_{10}$, $R_{11}$, $R_{12}$ and $R_{13}$ may combine and form a 5- or 6-membered carbocyclic ring. A suitable number of carbon atoms for the carbocyclic ring including substituent groups thereon or $R_{10}$, $R_{11}$, $R_{12}$ and $R_{13}$ is 3 to 15 carbon atoms, preferably 3 to 10 carbon atoms.

Typical examples of 5- and 6-membered carbocyclic rings include a cyclopentane ring, a cyclopentene ring, a cyclohexane ring, a cyclohexene ring and the like.

$Z_1$ and $Z_2$, which may be the same or different, each represents an atomic group necessary to form a saturated or unsaturated 5- and 6-membered ring. Moreover, the ring formed by $Z_1$ and $Z_2$ can be substituted with one or more substituents or can be condensed with another ring such as a saturated or unsaturated ring, e.g., a cyclohexene ring, a benzene ring or a naphthalene ring. Suitable examples of substituents which can be present on the ring formed by $Z_1$ and $Z_2$ include one or more of an alkyl group, an alkoxy group, an aryloxy group, a halogen atom (such as chlorine, bromine, fluorine and iodine), an aryl group, a hydroxy group, an amino group, an alkyl- or aryl-substituted amino group, an acyiamino group, a sulfonylamino group, a carbamoyl group, a sulfamoyl group, a carboxyl group, an alkoxycarbonyl group, an acyloxy group, a heterocyclic ring (such as a pyrrole ring, a furan ring, a piperidine ring, a morpholine ring, a pyridine ring, etc.) a cyano rgrup, a nitro group, and the like, and suitable examples of saturated or unsaturated rings condensed therewith include a cyclopentene ring, a cyclohexene ring, a benzene ring, a naphthalene ring, an anthracene ring, a phenanthrene ring, a thiopehne ring, a pyridine ring, etc.

Specific examples of heterocyclic rings formed by $Z_1$ and $Z_2$ include 5- and 6-membered heterocyclic rings such as those including nuclei comprising those of the thiazole series (e.g., thiazole, 4-methylthiazole, 4-phenylthiazole, 4,5-diphenylthiazole, 4,5-dimethylthiazole, etc.), those of the benzothiazole series (e.g., benzothiazole, 5-chlorobenzothiazole, 5-methylbenzothiazole, 5-phenylbenzothiazole, 5-methoxybenzothiazole, 4-fluorobenzothiazole, 5,6-dioxymethylenebenzothiazole, 5-nitrobenzothiazole, 5-trifluoromethylbenzothiazole, 5-methoxycarbonylbenzothiazole, 5-hydroxybenzothiazole, 6-hydroxybenzothiazole, 5-cyanobenzothiazole, 5-iodobenzothiazole, etc.), those of the naphthothiazole series (e.g., α-naphthothiazole, β-naphthothiazole, γ-naphthothiazole, 5-methoxy-β-naphthothiazole, 8-methoxy-α-naphthothiazole, 6-methoxy-8-acetyloxy-β-naphthothiazole, 8,9-dihydro-β-naphthothiazole, etc.), those of the oxazole series (e.g., 4-methyloxazole, 4,5-diphenyloxazole, 4-phenoxyoxazole, etc.), those of the benzoxazole series (e.g., benzoxazole, 5-chlorobenzoxazole, 5,6-dimethylbenzoxazole, 6-hydroxybenzoxazole, 5-phenylbenzoxazole, etc.), those of the naphthoxazole series (e.g., α-naphthoxazole, β-naphtoxazole, etc.), those of the selenazole series (e.g., 4-methylselenazole, 4-phenylselenazole, etc.), those of the benzoselenazole series (e.g., benzoselenazole, 5-chlorobenzoselenazole, 5-methoxybenzoselenazole, 5-hydroxybenzoselenazole, etc.), those of the thiazoline series (e.g., thiazoline, 4,4-dimethylthiazoline, etc.), those of the 2-pyridine series (e.g., 2-pyridine, 5-methyl-2-pyridine, 5-methoxy-2-pyridine, 4-chloro-2-pyridine, 5-carbamoyl-2-pyridine, 5-methoxycarbonyl-2-pyridine, 4-acetylamino-2-pyridine, 6-methylthio-2-pyridine, 6-methyl-2-pyridine etc.), those of the 4-pyridine series (e.g., 4-pyridine, 3-methoxy-4-pyridine, 3,5-dimethyl-4-pyridine, 3-chloro-4-pyridine, 3-methyl-4-pyridine, etc.), those of the 2-quinoline series (e.g., 2-quinoline, 6-methyl-2-quinoline, 6-chloro-2-quinoline, 6-ethoxy-2-quinoline, 6-hydroxy-2-quinoline, 6-nitro-2-quinoline, 6-acetylamino-2-quinoline, 6-dimethylaminocarbonyl-2-quinoline, 8-fluoro-2-quinoline, etc.), those of the 4-quinoline series (e.g., 4-quinoline, 6-methoxy-4-quinoline, 6-acetylamino-4-quinoline, 8-chloro-4-quinoline, 6-trifluoromethyl-4-quinoline, etc.), those of the 1-isoquinoline series (e.g., 1-isoquinoline, 6-methoxy-1-isoquinoline, 6-chloro-1-isoquinoline, etc.), those of the 3,3-dialkylindolenine series (e.g., 3,3-dimethylindolenine, 3,3,7-trimethylindolenine, 5-chloro-3,3-dimethylindolenine, 5-ethoxycarbonyl-3,3-dimethylindolenine, 5-nitro-3,3-dimethylindolenine, 3,3-dimethyl-4,5-phenyleneindolenine, 3,3-dimethyl-6,7-phenyleneindolenine, 5-acetylamino-3,3-dimethylindolenine, 5-diethylamino-3,3-dimethylindolenine, 5-methanesulfonylamino-3,3-dimethylindolenine, 5-benzoylamino-3,3-dimethylindolenine, etc.), those of the imidazole series (e.g., imidazole, 1-alkyl-4-phenylimidazole, 1-alkyl-4,5-dimethylimidazole, etc.), those of the benzimidazole series (e.g., benzimidazole, 1-alkylbenzimidazole, 1-alkyl-5-trifluorobenzimidazole, 1-alkyl-5-chlorobenzimidazole, 1-alkyl-5-sulfamoylbenzimidazole, 1-aryl-5-methoxycarbonylbenzimidazole, 1-alkyl-5-acetylaminobenzimidazole, 1-alkyl-5-nitrobenzimidazole, 1-alkyl-5-diethylaminobenzimidazole, 1-alkyl-5-pentyloxybenzimidazole, etc.), those of naphthimidazole series (e.g., 1-alkyl-α-naphthimidazole, 1-alkyl-5-methoxy-β-naphthimidazole, etc.) and like rings.

Suitable examples of substituents which can be present on the L, $L_2$ or $L_3$ substituted methine group include an alkyl group (e.g., methyl, ethyl, butyl, etc.), an aryl group (e.g., phenyl, tolyl, etc.), a halogen atom (e.g., chlorine, bromine, fluorine and iodine), or an alkoxy group (e.g., methoxy, ethoxy, etc.) and suitable rings formed by the combination of $L_1$ and $R_3$ include a 5-membered heterocyclic ring (e.g., a pyrroline ring, etc.) and a 6-membered heterocyclic ring (e.g., a tetrahydropyridine ring, an oxazine ring, etc.).

The term "pharmaceutically acceptable anion" for Q which is necessary for electrical charge balance in the compounds above is intended to mean an ion, when administered to the host subjected to the method of treatment of this invention, which is non-toxic and which renders the compounds above soluble in aqueous systems.

Suitable examples of pharmaceutically acceptable anions represented by Q include halides such as chloride, bromide and iodide, sulfonates such as aliphatic and aromatic sulfonates, e.g., methanesulfonate, trifluoromethanesulfonate, p-toluenesulfonate, naphthalenesulfonate, 2-hydroxyethanesulfonate, and the like, sulfamates such as cyclohexanesulfamate, sulfates such as methyl sulfate and ethyl sulfate, bisulfates, borates, alkyl and dialkyl phosphates such as diethyl phosphate and methylhydrogen phosphate, pyrophosphates such as trimethylpyrophosphate and diethyl hydrogen pyrophsophate, carboxylates, advantageously carboxy- and hydroxy-substituted carboxylates and carbonates. Preferred examples of pharmaceutically acceptable anions include chloride, bromide, iodide, acetate, propionate, valerate, citrate, maleate, fumarate, lactate, succinate, tartrate and benzoate.

In particular, rhodacyanine compounds of the Formulae (I) to (V) where $Y_1$ is a sulfur atom, $L_2$ and $L_3$ are unsubstituted methine group and anion represented by Q is chloride, bromide, iodide, p-toluenesulfonate or acetate are preferred.

The compounds of general Formulae (I) to (V) described above can be easily produced from known starting materials in accordance with the methods disclosed in British Patent Nos. 489,335 and 487,051; in U.S. Pat. Nos. 2,388,963, 2,454,629, 2,504,468, 2,536,986 and 2,961,318, the disclosure of which is incorporated herein by reference.

Typical examples of compounds of Formulae (I) to (V), the cation moiety of which has log P value of 4.5–12, which can be employed in this invention, include the following compounds; however, the present invention is not to be construed as being limited to these compounds.

| Compound No. | Structure |
|---|---|
| 1 | 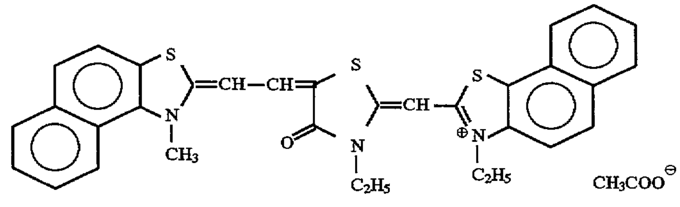 |

-continued

| Compound No. | Structure |
|---|---|
| 2 | (structure image) |
| 3 | (structure image) |
| 4 | (structure image) |
| 5 | (structure image) |
| 6 | (structure image) |
| 7 | (structure image) |
| 8 | (structure image) |

-continued

| Compound No. | Structure |
|---|---|
| 9 | 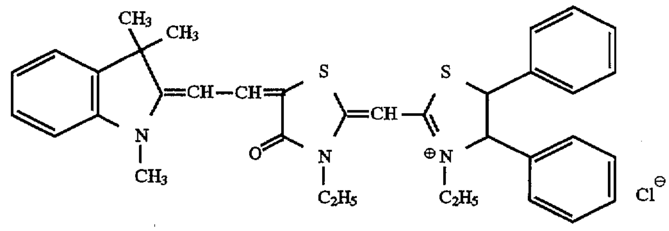 |
| 10 | 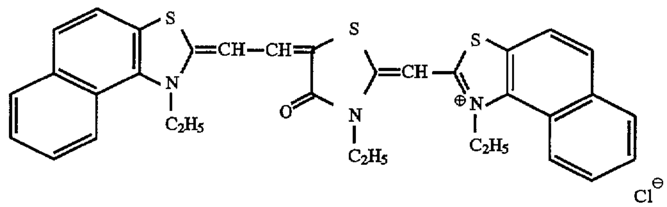 |
| 11 | 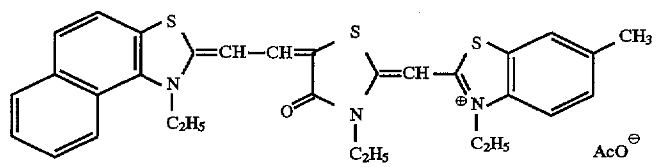 |
| 12 | 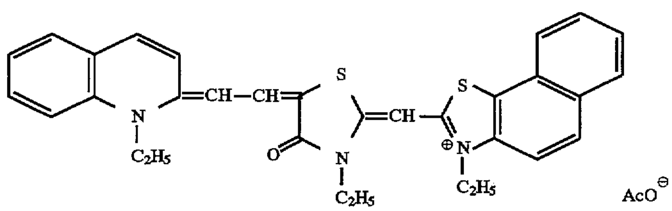 |
| 13 | 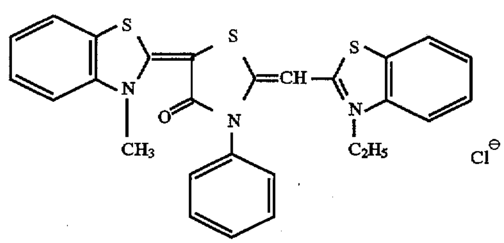 |
| 14 | 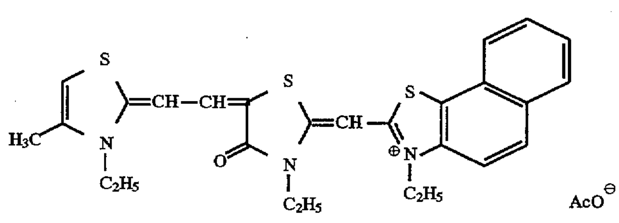 |
| 15 | 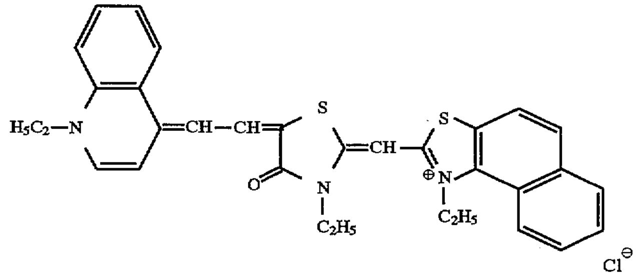 |

-continued
| Compound No. | Structure |
|---|---|
| 16 | 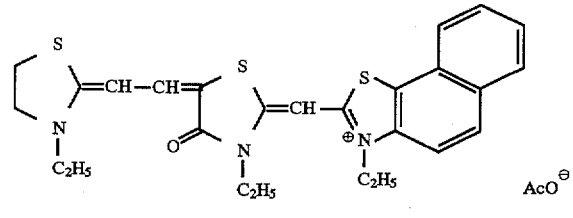 AcO⁻ |
| 17 | 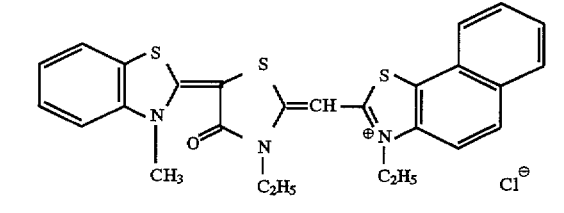 Cl⁻ |
| 18 | 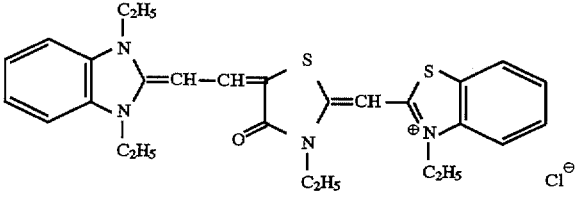 Cl⁻ |
| 19 | 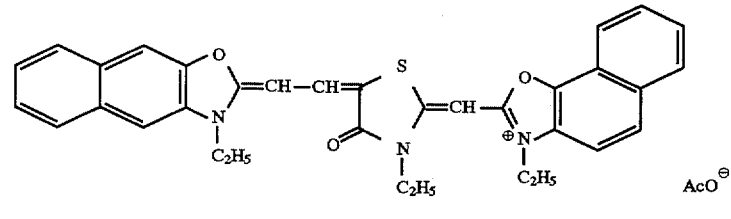 AcO⁻ |
| 20 | 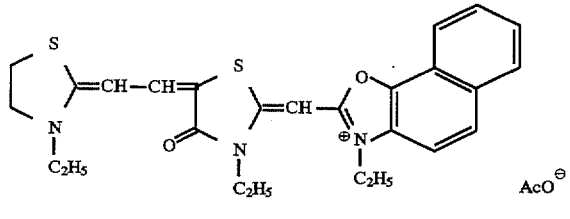 AcO⁻ |
| 21 | 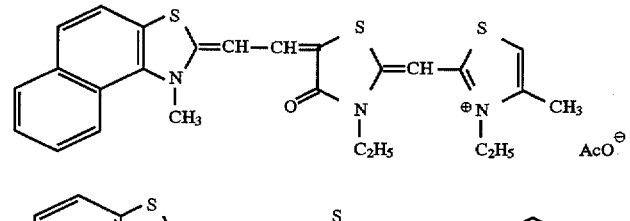 AcO⁻ |
| 22 | 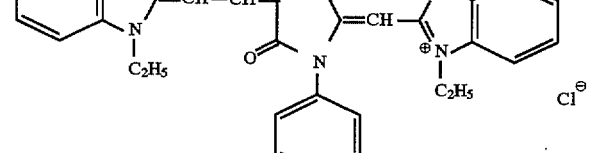 Cl⁻ |

-continued

| Compound No. | Structure |
| --- | --- |
| 23 | 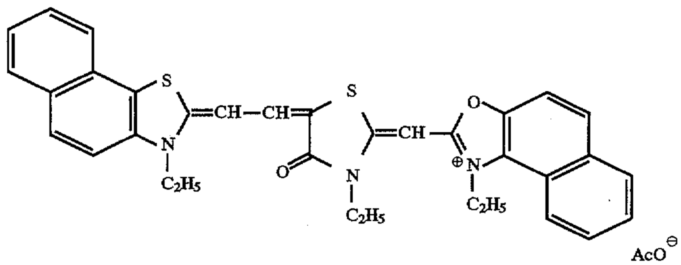 |
| 24 | 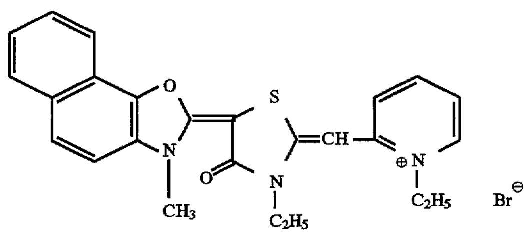 |
| 25 | 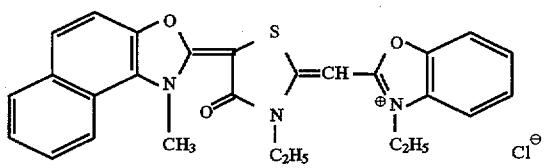 |
| 26 | 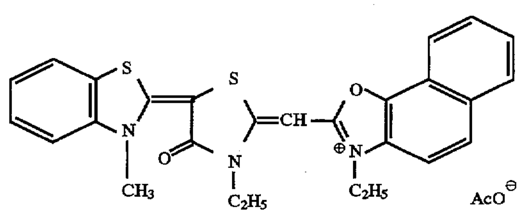 |
| 27 | 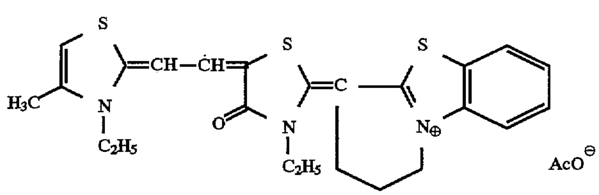 |
| 28 | 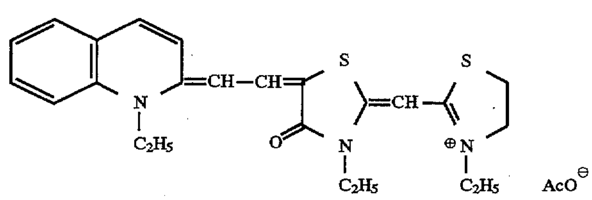 |
| 29 | 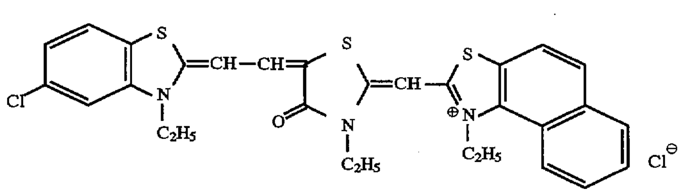 |

| Compound No. | Structure |
|---|---|
| 30 | (chemical structure) |
| 31 | (chemical structure) |
| 32 | (chemical structure) |
| 33 | (chemical structure) |
| 34 | (chemical structure) |
| 35 | (chemical structure) |
| 36 | (chemical structure) |
| 37 | (chemical structure) |

-continued
| Compound No. | Structure |
|---|---|
| 38 | 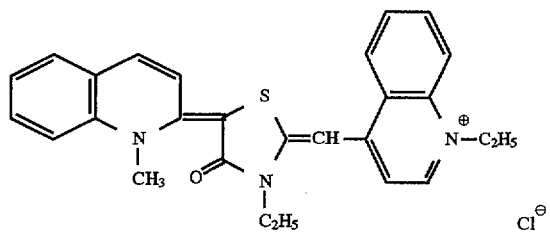 |
| 39 | 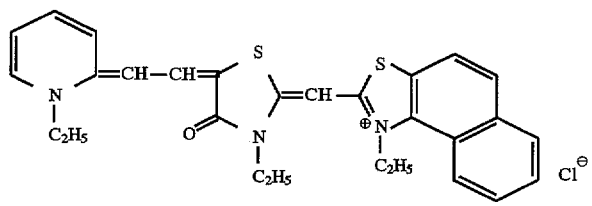 |
| 40 | 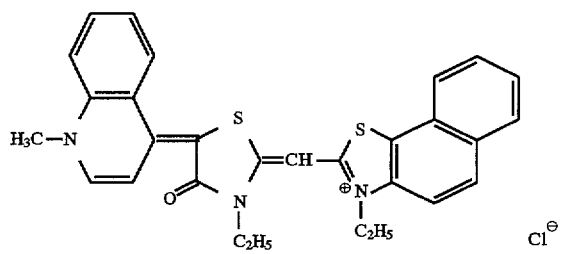 |
| 41 | 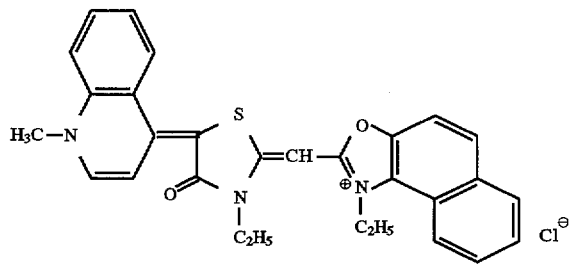 |
| 42 | 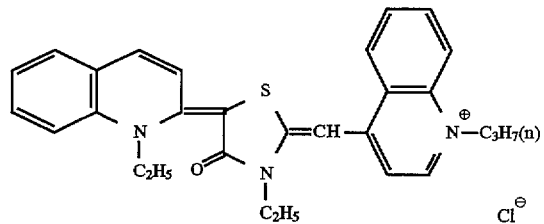 |
| 43 | 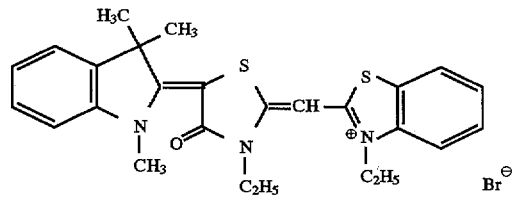 |

-continued
| Compound No. | Structure |
|---|---|
| 44 | 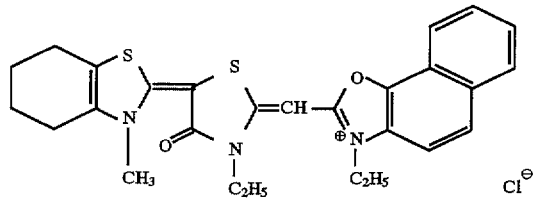 |
| 45 | 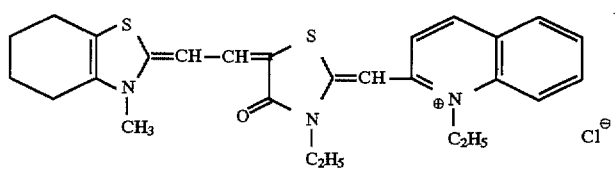 |
| 46 | 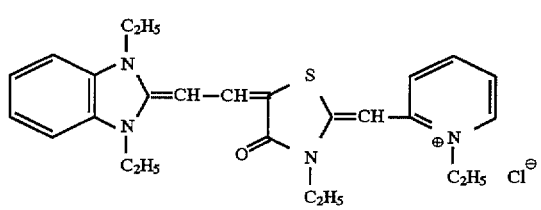 |
| 47 | 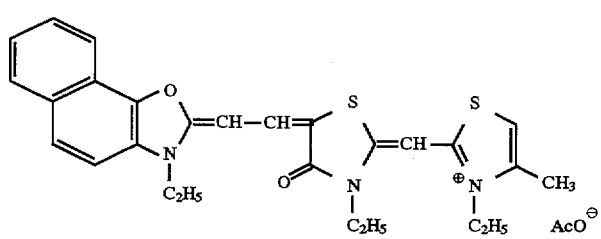 |
| 48 | 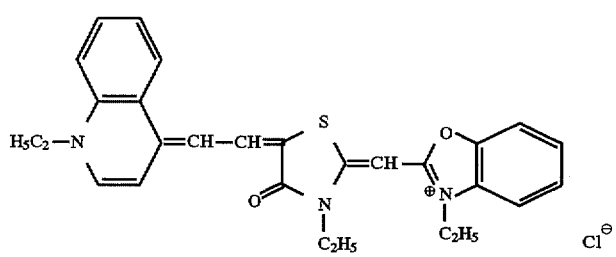 |
| 49 | 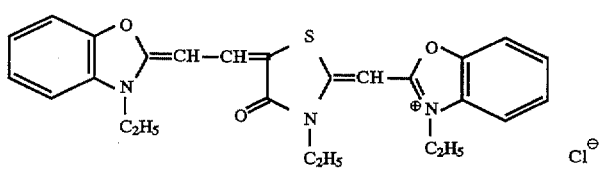 |
| 50 | 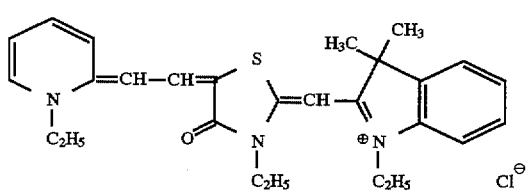 |
| 51 | 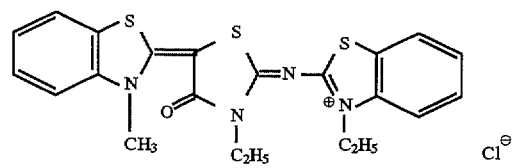 |

-continued

| Compound No. | Structure |
| --- | --- |
| 52 | 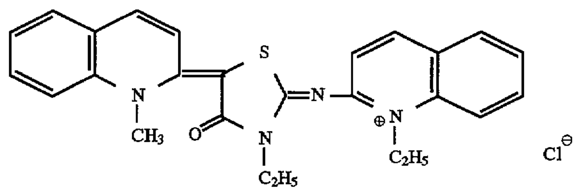 |
| 53 | 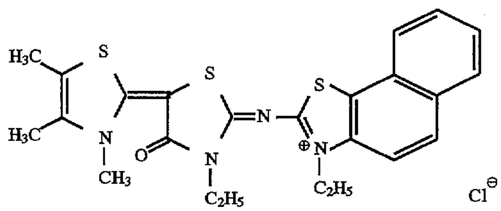 |
| 54 | 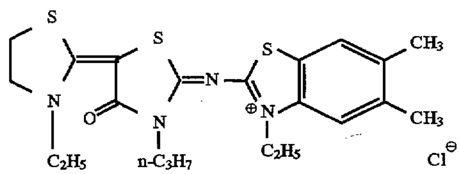 |
| 55 | 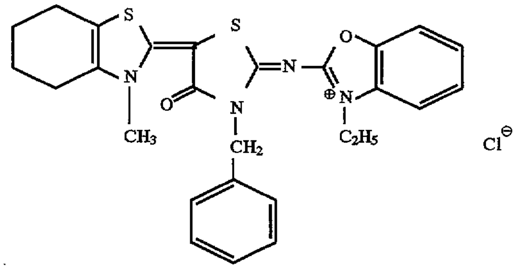 |
| 56 | 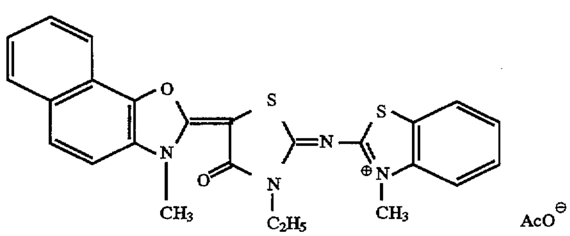 |
| 57 | 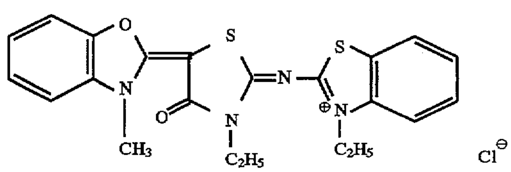 |
| 58 | 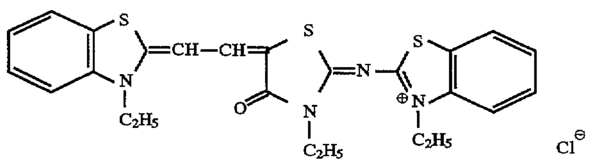 |

-continued
| Compound No. | Structure |
|---|---|
| 59 | 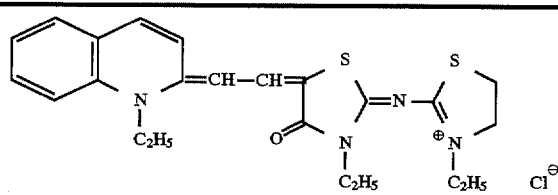 |
| 60 | 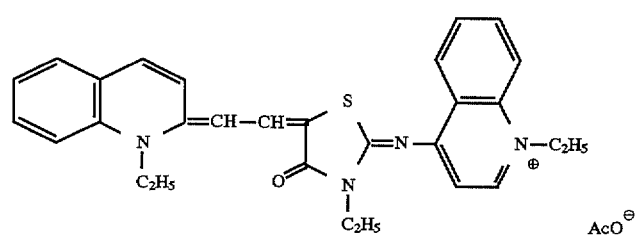 |
| 61 | 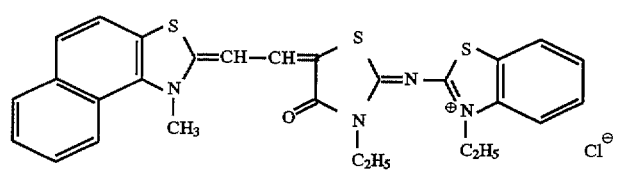 |
| 62 | 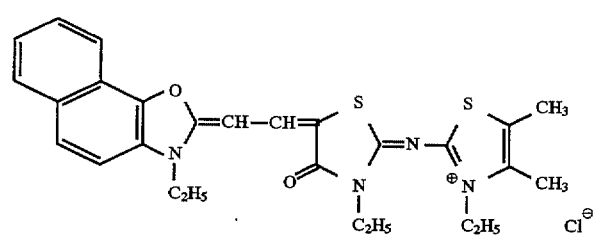 |
| 63 | 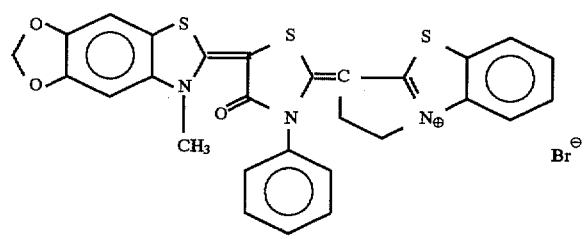 |
| 64 | 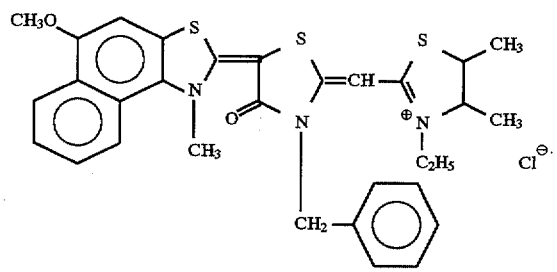 |
| 65 | 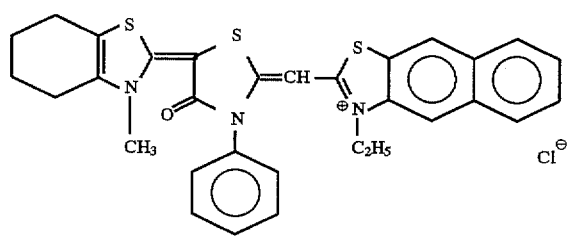 |

-continued
| Compound No. | Structure |
|---|---|
| 66 | 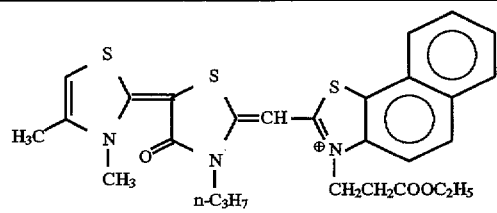 |
| 67 | 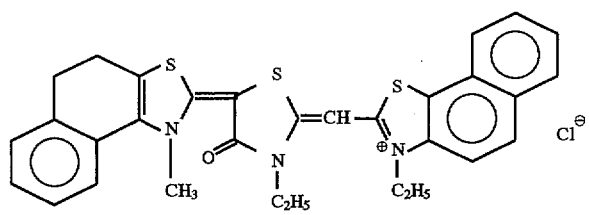 |
| 68 | 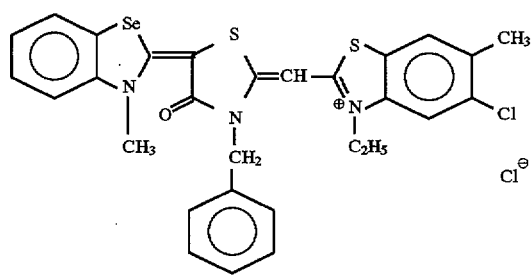 |
| 69 | 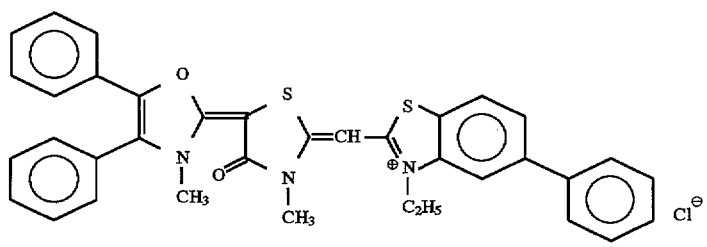 |
| 70 | 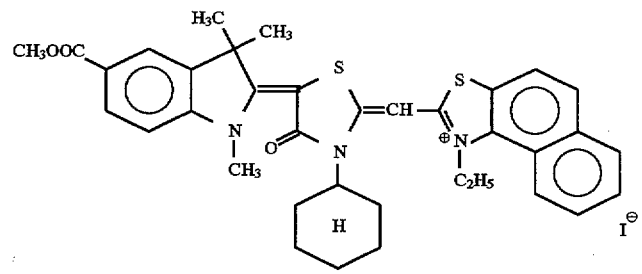 |
| 71 | 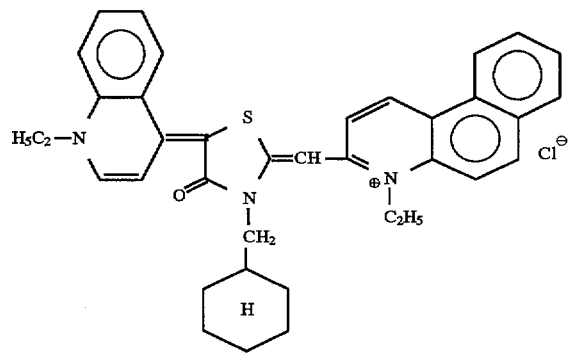 |

-continued
| Compound No. | Structure |
|---|---|
| 72 | 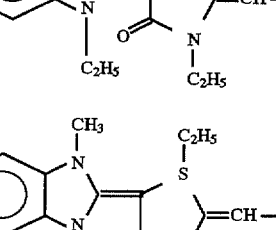 |
| 73 | 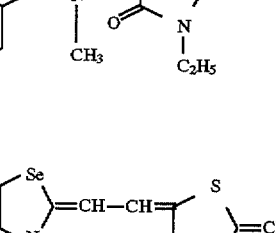 |
| 74 | 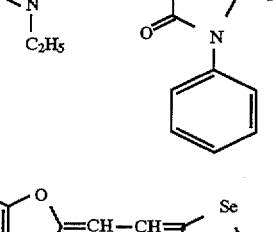 |
| 75 | 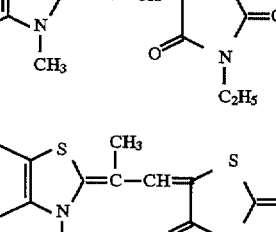 |
| 76 | 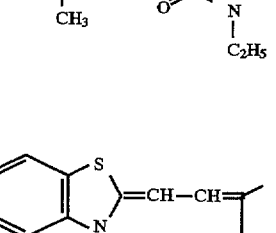 |
| 77 | 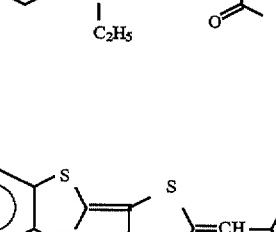 |
| 78 | 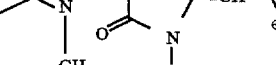 |

-continued

| Compound No. | Structure |
|---|---|
| 79 | 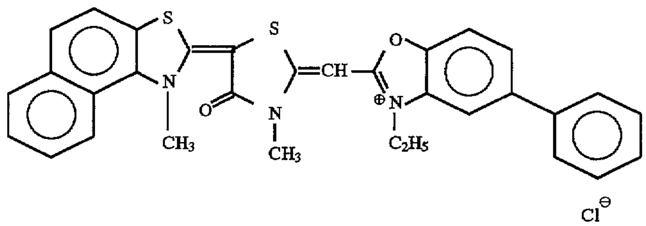 |
| 80 | 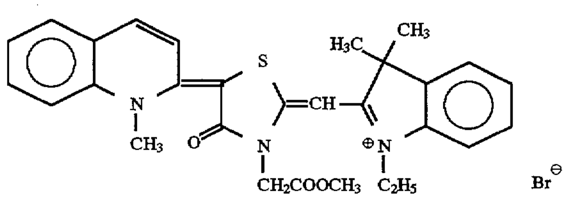 |
| 81 | 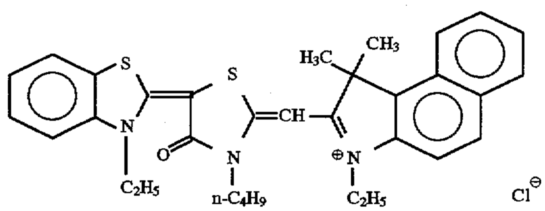 |
| 82 | 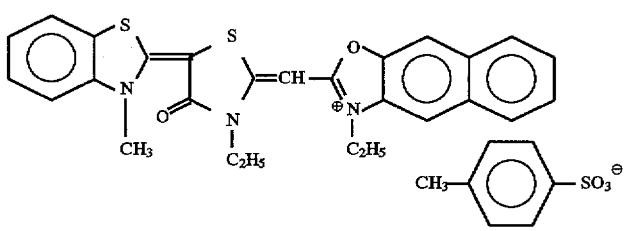 |
| 83 | 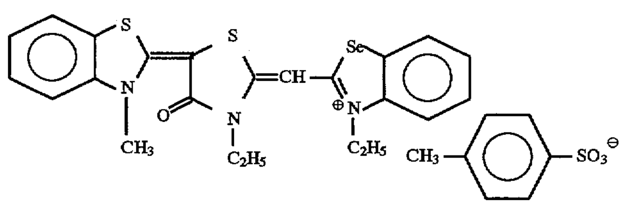 |
| 84 | 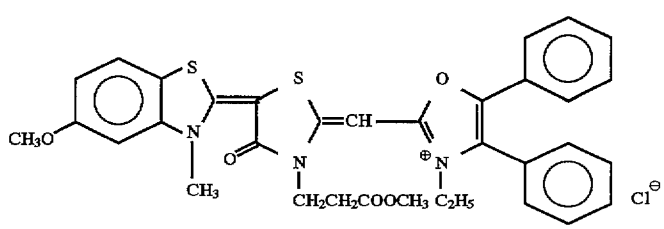 |

-continued

| Compound No. | Structure |
|---|---|
| 85 | 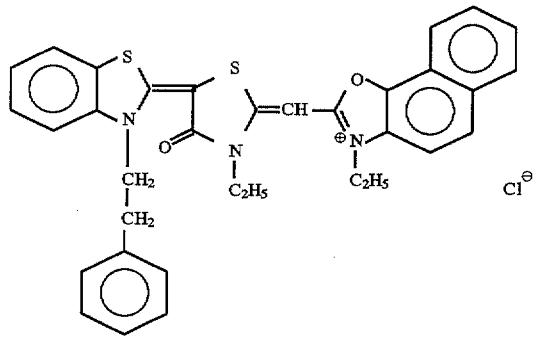 |
| 86 | 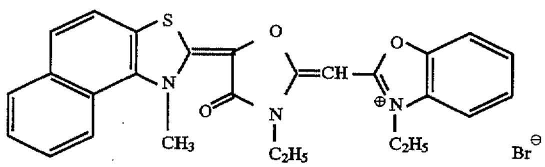 |
| 87 | 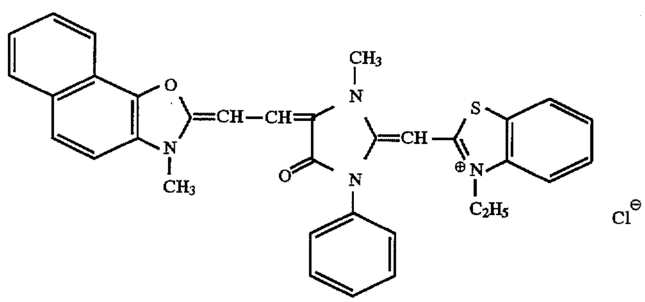 |
| 88 | 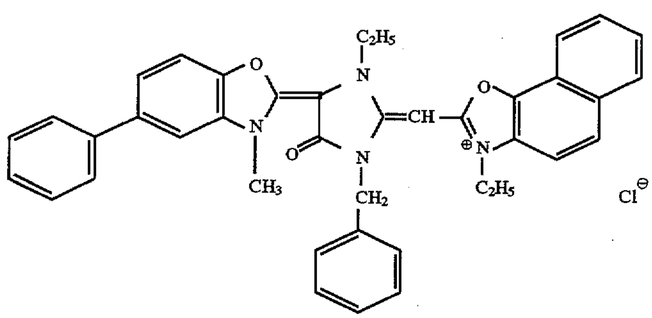 |
| 89 | 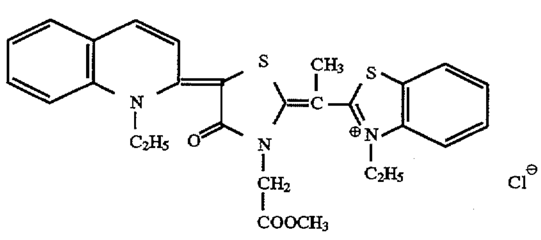 |
| 90 | 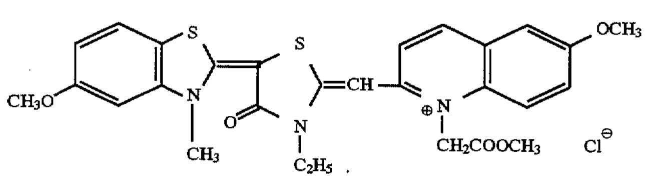 |

| Compound No. | Structure |
|---|---|
| 91 | 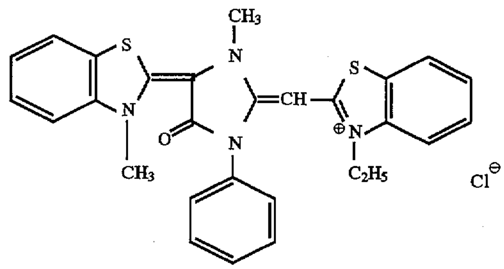 |
| 92 | 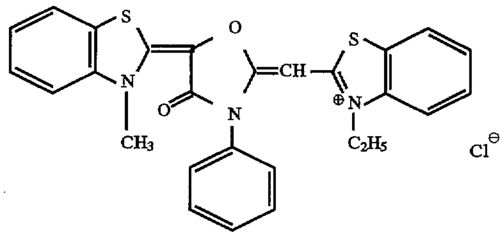 |
| 93 | 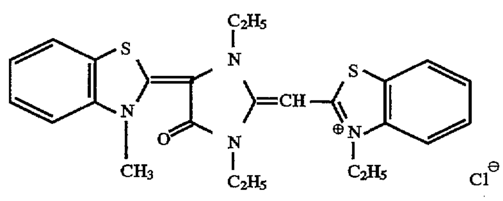 |
| 94 | 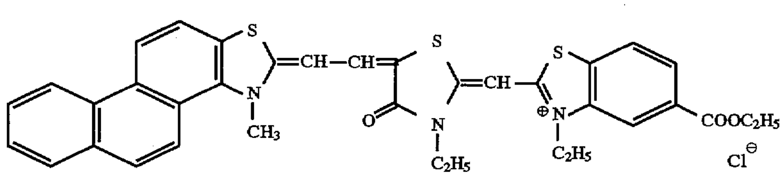 |
| 95 | 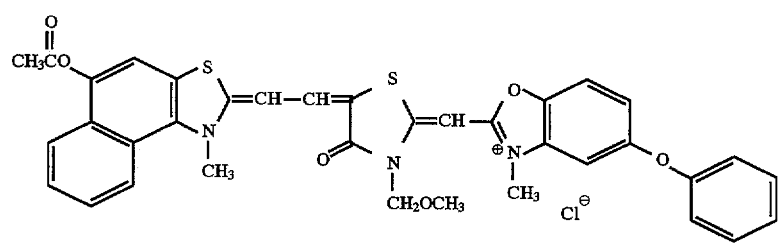 |
| 96 | 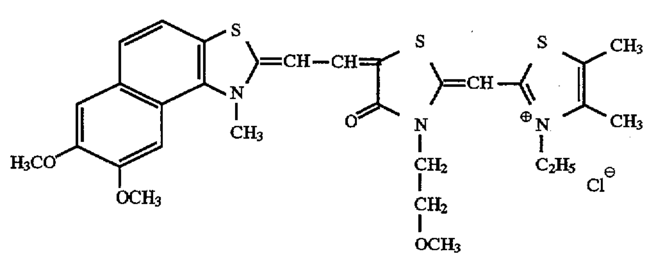 |

The compounds of the Formula (I), the cation moiety of which has log P value of 4.5–12, especially 5–11, are contained in the anti-cancer compositions of this invention in the form of rhodacyanine-cyclodextrin complex.

Examples of the cyclodextrins usable in the present invention for improving the solubility of the rhodacyanine compound of the Formula (I) include various types of cyclodextrin such as α-cyclodextrin, β-cyclodextrin, γ-cyclodextrin (hereafter referred to as α-CD, β-CD and γ-CD, respectively) and are prepared by reacting starch or dextrin with amylase.

For the anti-cancer composition of this invention, cyclodextrin derivatives such as those substituted by various substituents to improve the physical properties or functional characteristics thereof can also be employed, as well as the above cyclodextrins. Among these, cyclodextrin derivatives derived from β-CD are preferred. Examples of β-CD derivatives include β-CD disubstituted with a alkyl group having 1 to 4 carbon atoms or a hydroxyalkyl group having 1 to 24 carbon atoms. Specific examples of β-CD derivatives include dimethyl-β-cyclodextrin (DM-β-CD), hydroxypropyl-β-cyclodextrin (HP-β-CD) and dihydroxypropyl-β-cyclodextrin (DHP-β-CD). These β-CD derivatives are expected to be effective as material for formulation of pharmaceutical composition since they are of excellent water-solubility, functional characteristics and safety.

Preferred cyclodextrins and derivatives thereof which can be used with rhodacyanine compound of the Formulas (I) are β-CD, γ-CD, HP-β-CD and DHP-β-CD, more preferably, γ-CD and HP-β-CD.

The anti-cancer composition of this invention, which comprises rhodacyanine compound represented by the Formula (I) and cyclodextrin or derivarive thereof, can be effectively used to treat various types of cancer including melanomas, hepatomas, gliomas, neuroblastomas, sarcomas and carcinomas of the lung, colon, breast, bladder, ovary, testis, prostate, cervix, pancreas, stomach, small intestine and other organs.

The anti-cancer compositions of this invention can contain one or more compounds of the Formula (I), if desired, in combination with other therapeutic agents including conventional anti-tumor agents known in the art in the form of a complex with one or more cyclodextrins or derivatives thereof. Suitable examples of such conventional anti-tumor agents which can be used include adriamycin, cisplatin, colchicine, CCNU (Lomastine), BCNU (Carmustine), Actinomycin D, 5-fluorouracil, thiotepa, cytosinearabinoside, cyclophosphamide, mitomycin C, and the like.

Further, the anti-cancer compositions of this invention can contain pharmaceutical carrier solvents and can also contain additional carriers and/or solubilizers sucu as surface active agents other than the rhodacyanine-cyclodextrin complex.

Suitable examples of the pharmaceutical carrier solvents which can be employed include water for injection, glucose aqueous solution, saline solution, dextrose aqueous solution and a mixture of polyol and ethanol such as polyethoxy castor oil which is available under the designation "Dilnent No.12" from National Cancer institute in USA. Preferred carrier solvents is water for injection.

Suitable examples of the additional carriers include gelatin; natural sugars such as sucrose and lactose; lecithin; pectin; starch such as corn starch; alginic acid; tylose; talc; lycopodium; silicas such as colloidal silica; cellulose; cellulose dereivatives such as cellulose ether, hydroxyl groups of which are partially etherified with lower aliphatic alcohol and/or lower saturated oxyalcohol, e.g., methyl hydroxypropyl cellulose, methyl cellulose and hydroxyethyl cellulose; monohydric or polyhydric alcohols and polyglycols such as glycerine, mannitol, sorbitol, pentaerythritol, ethyl alcohol, diethylene glycol, triethylene glycol, ethylene glycol, propylene glycol, dipropylene glycol, polyethylene glycol 400 and other polyethylene glycol derivatives; esters of saturated and unsaturated fatty acids, e.g., having 2 to 22 carbon atoms, especially 10 to 18 carbon atoms, with monohydric aliphatic alcohols (e.g., having 1 to 20 carbon atoms such as alkanols) or polyhydric alcohols such as glycols, glycerine, diethylene glycol, pentaerythritol, sorbitol, mannitol, ethyl alcohol, butyl alcohol, octadecyl alcohol, such as glyceryl monostearate, glyceryl monopalmitate, glycol distearate, glycol dilaurate, glycol diacetate, monoacetin, triacetin, glyceryl oleate, ethylene glycol stearate, esters with etherified polyhydric alcohols; benzyl benzoate; dioxolan; glycerine formal; tetrahydrofurfuryl alcohol; polyglycol ether of alcohol having 1 to 12 carbon atoms; dimethylacetamine; lactam; lactate such as ethyl lactate and ethyl carbonate; silicone, especially dimethylpolysiloxane having a intermediate viscosity and the like.

The other additional carriers are described in, for example, U.S. Pat. No. 4,598,091, the disclosure of which is incorporated herein by reference.

In the case where the anti-cancer composition of this invention is used as an injection, the concentration of a compound of the Formula (I) contained in the injection is about 0.0001% by weight to about 10% by weight, more generally about 0.001% by weight to about 1% by weight, based on the total weight of the composition, and a suitable molar proportion of the compound of the Formula (I) to cyclodextrin or derivative thereof for forming the complex is $1/10$–$1/500$, preferably $1/2$–$1/20$.

The injection may be prepared by adding cyclodextrin to a mixture of the compound of the Formula (I) and carrier solvent mentioned above, or by adding the compound of the Formula (I) to a solution of cyclodextrin in the carrier solvent. The injection may also be prepared by dissolving the compound of the Formula (I) in an aqueous solution of cyclodextrin and then adding an additional carrier solvent to the solution. Further, the injection may also be prepared by adding water to a mixture of compound of the Formula (I), cyclodextrin and the additinal carrier mentioned above. The concentration of the additinal carrier in the injection should be adjusted to yield a predetermined osmotic pressure.

The concentration of cyclodextrin or derivative thereof in the injection may be optionally determined according to the solubility of cyclodextrin per se as well as the compound of the Formula (I) in the carrier solvent used for the injection. However, it is normally about 0.1% by weight to about 50% by weight, preferably about 0.5% by weight to about 45% by weight, based on the weight of the injection.

Preparation of the injection is carried out at a temperature varying according to both the stability and solubility of the compound of the Formula (I). However, it is normally carried out at a temperature of 0° C. to 95° C., preferably 5° C. to 60° C. The time period for dissolving the compound of the Formula (I) with cyclodextrin also varies according to the solubility of the compound of the Formula (I), however it normally ranges from several minutes to several hours. The dissolving process is carried out by means of, for example, supersonication, agitation, shaking or the like. Other additives and preparation processes for the anti-cancer compositions of this invention are described in, for example, U.S. Pat. No. 4,598,091, the disclosure of which is incorporated herein by reference.

The injection may be prepared just before the administration thereof, or packaged in an appropriate bottle such as ampul or vial and then stored untill it will be used for an administration.

Suitable modes of administration of the pharmaceutical composition of this invention include intravenous, intraperitoneal, intramuscular, subcutaneous, intratumor or intravesicular injection.

The pharmaceutically effective amount of the compound of the Formula (I) in the injection of this invention which can be employed will be dependent upon the nature of the cancer, the therapy sought, the severity of the disease, the degree of malignancy, the extent of metastatic spread, the tumor load, general health status, body weight, age, sex, and the (genetic) racial background of the patient. Again, as noted above, pharmaceutically effective amounts will be generally determined on the basis of the clinical symptoms observed and degree of progression of disease and like factors but a suitable therapeutically effective amount of the compound of the Formula (I) generally can range from b 0.01mg to 30 mg, more generally 0.05 mg to 20 mg, administered per day per 70 kg of body weight, in single or multiple doses, as determined appropriate for the therapy involved.

Other suitable modes of administration of the pharmaceutical composition of this invention include intra-arterial, peroral, percutaneous, and intrarectal administration.

This invention will be better understood by reference to the following Examples, include a preferred embodiment of this invention, but are not intended to restrict the scope of the claims appended hereto.

EXAMPLE 1

Solubilizers, β-CD, polyethylene glycol 400 and Pluronic F60, were added to demineralized water respectively to prepare solutions having concentrations shown in TABLE 1. 2 ml of each of the solutions was then added into individual 5 ml test tubes containing Compound 1. The test tubes were fixed in thermostatic bath controlled at 25° C. and allowed to stand for 24 hours. Then, the resulting solutions were filtered through a microfilter having pore size 0.45 μm and then amounts of Compound 1 dissolved in the filtrates were determined by measuring concentrations of Compound 1 using spectrophotomeric analysis. The results obtained are shown in TABLE 1 below. TABLE 1 shows that β-CD is the most effective solubilizer of the three in improving solubility of Compound 1, so that it increases the solubility of the compound itself in water by 4.4 times.

TABLE 1

Solubility of compound 1 in aqueous solution containing various solubilizers

| Solubilizer | Conc. of Solubilizer w/v % | Solubility mg/ml |
|---|---|---|
| β-CD | 1.5 | 8.17 |
| Polyethylene glycol 400 | 50 | 0.870 |
| Pluronic F60 | 0.02 | 3.23 |
| Pluronic F60 | 0.2 | 3.13 |
| water only | 0.0 | 1.86 |

EXAMPLE 2

Solutions of HP-β-CD in demineralized water having concentrations varying from 0 w/v % to 45 w/v % were prepared as described in EXAMPLE 1. Compound 1 was then dissolved in each of the aqueous solutions to prepare a saturate solution of Compound 1. 70 μl of each of the resulting solutions was added to 1 ml of rat serum and fetal calf serum respectively and, after shaking, the mixtures were stood for 30 minutes at 25° C. while shutking a light. The mixtures were filtered through a microfilter having pore size 0.45 μm and then amounts of Compound 1 dissolved in the filtrates were determined by measuring concentrations of Compound 1 using spectrophotomeric analysis. The results obtained are shown graphically in FIGS. 1 and 2. FIGS. 1 and 2 show that Compound 1 is much dissolved in the serums, depending on the increase in HP-β-CD concentration.

EXAMPLE 3

Solubility of Compound 1 in each of aqueous solutions of β-CD, HP-β-CD and γ-CD was determined in the same manner as described in EXAMPLE 2. The results obtained are shown graphically in FIG. 3. FIG. 3 shows that all cyclodextrin compounds used improve solubility of Compound 1 in water, in particular γ-CD greatly improves the solubility.

EXAMPLE 4

Aqueous solutions of β-CD, HP-β-CD and γ-CD were prepared and solubility of Compounds 2, 4 and 5 in each of the aqueous solutions having the concentration varing as shown in TABLE 2 was determined as described in EXAMPLE 2. For the purpose of comparison, solubility of Compounds 2, 4 and 5 in water was also determined. The results were shown in TABLE 2 below. TABLE 2 shows that solubility of Compounds 2, 4 and 5 in water is improved by all of the cyclodextrin compounds used.

TABLE 2

Solubility of Compound 2, 4 and 5 in aqueous solution containing various cyclodextrin compounds

| | | Aqueous solution of CD | | Water |
|---|---|---|---|---|
| Compound No. | CD | Conc. of CD mM/dl | Solubility mM/dl | Solubility mM/dl |
| 2 | β-CD | 0.80 | 0.55 | 0.03 |
| 4 | HP-β-CD | 4.2 | 0.03 | 0.001 |
| 5 | γ-CD | 1.0 | 0.02 | ~0 |

EXAMPLE 5

1 ml of rat bloods containing sodium citrate as an anticoagulating agent each was added into individual test tubes and then 70 μl of aqueous solutions of Compound 1 and HP-β-CD having ratio shown in TABLE 3 each was added to individual test tubes and the resulting mixtures were shaken. After shaking, one droplet of each of the mixtures was put on a slide glass to observe the occurrence of precipitation of Compound 1 using a microscope with 100–400× magnification. The results obtained are shown in TABLE 3 below. TABLE 3 shows that when HP-β-CD concentration increases, precipitation of Compound 1 in blood is effectively inhibited in every case where concentrations of Compound 1 were varied.

TABLE 3

Effect of HP-β-CD on the solubility of Compound 1 in rat blood

| | State of precipitation Compound 1 concentration | | | |
|---|---|---|---|---|
| Conc. of HP-β-CD w/v % | 3 mg/ml | 2 mg/ml | 1 mg/ml | 0.6 mg/ml |
| 2.25 | +++ | ++ | + | (+) |
| 4.5 | +++ | ++ | + | (+) |
| 9.0 | ++ | + | (+) | − |
| 18 | + | − | − | − |
| 36 | − | − | − | − |
| 45 | − | − | − | − |

(+): precipitate of Compound 1 was not observed by macroscopy, but was observed by microscopic observation.
+—+++: Precipitate was observed by macroscopy.
−: Precipitate was not observed by macroscopy and microscopy.

EXAMPLE 6

Rhodacyanine compounds, the cation moiety of which has log P value shown in TABLE 4, were dissolved in 45% HP-β-CD aqueous solution, 45% DHP-β-CD aqueous solution or 10% γ-CD aqueous solution to yield the compound concentration of 3 mg/ml. 70 µl of the solutions were added to 1 ml of individual rat bloods containing sodium citrate as an anti-coagulating agent and the resulting mixtures were shaken as described in EXAMPLE 5. After shaking, one droplet of each of the mixtures was put on a slide glass to observe the occurrence of precipitation of the rhodacyanine compound using a microscope with 100–400× magnification. As a result, no precipitate was observed for all samples.

On the other hand, the rhodacyanine compounds shown in TABLE 4 were tested using the protocol described above except that water was used instead of cyclodextrin aqueous solution and the concentration of the rhodacyanine compound was changed to 1 mg/ml from 3 mg/ml. In these cases, precipitate was observed for all samples, contrary to the above-mentioned results.

These results show that cyclodextrin compounds used in this example inhibit effectively precipitation of the rhodacyanine compounds, the cation moiety of which has log P value not less than 4.5 in rat serum.

TABLE 4

| Compound No. | log P | Aqueous solution of CD |
|---|---|---|
| 1 | 8.89 | A |
| 2 | 5.05 | B |
| 3 | 5.42 | A |
| 4 | 6.11 | A |
| 5 | 8.51 | B |
| 6 | 7.98 | A |
| 7 | 5.42 | C |
| 8 | 7.15 | A |
| 9 | 8.66 | A |
| 10 | 9.41 | A |
| 11 | 8.65 | A |
| 12 | 8.43 | C |
| 13 | 6.86 | B |
| 14 | 5.97 | A |
| 15 | 7.85 | C |
| 16 | 5.82 | A |
| 17 | 7.23 | B |
| 18 | 6.93 | A |
| 19 | 8.34 | A |
| 20 | 5.29 | C |
| 21 | 5.95 | C |
| 22 | 7.76 | B |
| 23 | 8.88 | A |
| 24 | 5.42 | C |
| 25 | 6.16 | A |
| 26 | 6.70 | A |
| 27 | 6.70 | B |
| 28 | 5.05 | C |
| 29 | 8.87 | A |
| 30 | 5.95 | A |
| 31 | 5.95 | B |
| 32 | 7.23 | A |
| 33 | 6.94 | A |
| 34 | 7.23 | A |
| 35 | 6.70 | A |
| 36 | 5.57 | A |
| 37 | 7.44 | C |
| 38 | 6.25 | A |
| 39 | 6.35 | A |
| 40 | 6.95 | B |
| 41 | 6.42 | C |
| 42 | 7.29 | A |
| 43 | 6.56 | C |
| 44 | 5.74 | C |
| 45 | 5.37 | A |
| 46 | 5.66 | A |
| 47 | 5.93 | A |
| 48 | 6.04 | A |
| 49 | 5.79 | B |
| 50 | 5.68 | B |
| 51 | 6.18 | C |

TABLE 4-continued

| Compound No. | log P | Aqueous solution of CD |
|---|---|---|
| 52 | 6.48 | C |
| 53 | 5.82 | A |
| 54 | 5.72 | B |
| 55 | 6.64 | C |
| 56 | 6.40 | B |
| 57 | 5.65 | C |
| 58 | 7.08 | A |
| 59 | 5.28 | A |
| 60 | 7.38 | A |
| 61 | 7.84 | A |
| 62 | 6.68 | A |
| 91 | 6.26 | C |
| 92 | 6.14 | C |
| 93 | 5.52 | C |

A: 45% HP-β-CD
B: 45% DHP-β-CD
C: 10% γ-CD

EXAMPLE 7

HP-β-CD was added to aqueous solutions of Compound 1 (3 mg/ml) to yield HP-β-CD concentrations varying from 2.25 w/v % to 45 w/v %. Each of the resulting solutions was intravenously injected into ICR mice (male, aged 6 weeks) at their tails in single dose of 5 ml per 1 kg of body weight and the mice were observed for their symptomes due to precipitation of Compound 1 in their bodies after injecting. After one day, the mice were dissected and their lungs were observed for precipitation of Compound 1. The results obtained are shown in TABLE 5 below. TABLE 5 shows that when HP-β-CD concentration increases, precipitation of Compound 1 in lung is effectively inhibited and at the same time toxity due to precipitation of Compound 1 is reduced.

TABLE 5

| Symptom and precipitation in lung after administration | | | | | | |
|---|---|---|---|---|---|---|
| Conc. of HP-β-CD | Animal 1 | | Animal 2 | | Animal 3 | |
| w/v % | symp. | preci. | symp. | preci. | symp. | preci. |
| 2.25 | died | +++ | died | +++ | angor | +++ |
| 4.5 | angor | +++ | angor | +++ | angor | +++ |
| 9.0 | (—) | +++ | (—) | +++ | (—) | ++ |
| 18 | (—) | +++ | (—) | + | (—) | + |
| 36 | (—) | − | (—) | − | (—) | − |
| 45 | (—) | − | (—) | − | (—) | − |

(—); No symptom was observed.
+++; Much precipitate was observed.
++; Precipitate was observed.
+; A little precipitate was observed.
+; No precipitate was observed.

EXAMPLE 8

To demonstrate a superiority of anti-cancer composition of the present invention, drug treatment tests were carried out by intraperitoneally injecting into mice solution of Compound 1 containing or not containing HP-β-CD.

2,500,000 human colon carcinoma cells (CX-1) were injected subcutaneously into each nude mouse (Swiss nu/nu) obtained from Taconic Farm and the mice were randomly allocated into a control group (five mice) and treatment groups (five mice per group).

The anti-cancer compositions containing HP-β-CD were prepared using the following method. HP-β-CD (45 g) was mixed with 100 ml of sterilized, double distilled water and stirred for four hours. Each of the compounds to be tested (20 mg) was mixed with 10 ml of HP-β-CD solution and sonicated for 60 minutes in the dark. This solution was then diluted in 5% glucose to yield a final compound concentration of 0.5 mg/ml, and further sonicated for 60 minutes in the dark to assure that the compound was completely dissolved. The anti-cancer compositions not containing HP-β-CD were also prepared using the same method except that 5% glucose solution was used instead of the HP-β-CD solution.

Drug treatment were performed according to the doses and schedules shown in TABLE 6. The control group received an equivalent volume of 5% glucose solution.

When the growth of tumors in the control group reached the exponential phase and the size of the tumor was palpable (usually 20 to 30 days after tumor implantation), the experiments were terminated. Tumors in each mouse were excised and weighed using an analytical balance. Total tumor weight in each group from five mice was calculated. Per cent tumor inhibition between the treated group and the control group was then calculated for each group. The results obtained are shown in TABLE 6 below.

TABLE 6 shows that a solution of Compound 1 containing HP-β-CD exhibits higher tumor inhibition than that containing no HP-β-CD.

TABLE 6

| Dose (mg/kg) | HP-β-CD | Schedule (i.p. on day) | Tumor Inhibition (%) |
| --- | --- | --- | --- |
| 2 | added | 1, 2, 4, 6, 7, 8, 9 | 48.8 |
| 2 | non-added | 1, 2, 4, 6, 7, 8, 9 | 29.1 |
| 4 | added | 1, 2, 4, 6, 7, 8, 9 | 30.2 |
| 4 | non-added | 1, 2, 4, 6, 7, 8, 9 | 20.9 |

EXAMPLE 9

To further demonstrate the uniqueness of the present invention, Compounds 7 and 8 were tested using the protocol described in EXAMPLE 8 except that the human melanoma LOX cell line was used instead of the human colon carcinoma cell line CX-1. For the solutions containing or not containing HP-β-CD prepared using the method described in EXAMPLE 8, T/C values were caluculated and the results obtained are shown in TABLE 7 below. T/C is the ratio, expressed as a percentage of the mean survival age of the treated group to the mean survival age of the untreated control group.

TABLE 7 shows that a solution of rhodacyanine compound containing HP-β-CD gives higher T/C value, i.e., exhibits macrobiotic effect than that containing no HP-β-CD.

TABLE 7

Survival rate (%) of Nude mice implanted with human melanoma LOX

| Comp. No. | Dose (mg/kg) | HP-β-CD | Schedule (i.p. on day) | T/C (%) |
| --- | --- | --- | --- | --- |
| 7 | 10 | added | 1, 4, 8, 12, 16, 21, 25 | 200 |
| 7 | 10 | non-added | 1, 4, 8, 12, 16, 21, 25 | 175 |
| 8 | 20 | added | 1, 2, 3, 4, 8, 9 | 227 |
| 8 | 20 | non-added | 1, 2, 3, 4, 8, 9 | 183 |

What is claimed is:

1. An anti-cancer composition for treating a cancer sensitive to a rhodacyanine compound represented by formula (I), wherein said anti-cancer composition comprises therapeutically effective amounts of (a) a rhodacyanine compound and (b) a cyclodextrin, and wherein said rhodacyanine compound (a) is selected from the group consisting of compounds represented by the following Formula (I), the cation moiety of which has a log P value of 4.5–12:

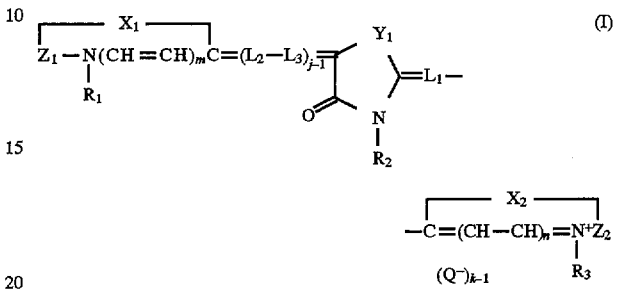

wherein $X_1$ and $X_2$, which may be the same or different, each represents O, S, Se,

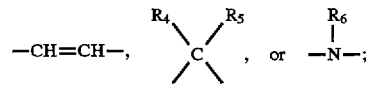

$Y_1$ represents O, S, Se, or

$R_1$ and $R_3$, which may be the same or different, each represents an alkyl group;

$R_2$ represents an alkyl group, an aryl group or a heterocyclic group;

$Z_1$ and $Z_2$, which may be the same or different, each represents an atomic group necessary to form a saturated or unsaturated 5- or 6-membered ring selected from the group consisting of a thiazole ring, a benzothiazole ring, a naphthothiazole ring, an oxazole ring, a benzoxazole ring, a naphthoxazole ring, a selenazole ring, a benzoselenazole ring, a thiazoline ring, a 2-pyridine ring, a 4-pyridine ring, a 2-quinoline ring, a 4-quinoline ring, a 1-isoquinoline ring, a 3,3-dialkylindolenine ring, an imidazole ring, a benzimidazole ring and a naphthimidazole ring;

$L_1$, $L_2$ and $L_3$, which may be the same or different, each represents a methine group or a nitrogen atom and $L_1$ and $R_3$ may combine and form a 5- or 6-membered ring;

$R_4$ and $R_5$, which may be the same or different, each represents an alkyl group;

$R_6$ and $R_7$, which may be the same or different, each represents an alkyl group or an aryl group;

Q represents a pharmaceutically acceptable anion;

j and k, which may be the same or different, each represents 1 or 2; and m and n, which may be the same or different, each represents 0 or 1, wherein said amounts are effective to enhance the solubility of (a).

2. The composition of claim 1, wherein the log P value of the cation moiety of the rhodacyanine compound is 5–11.

3. The composition of claim 1, wherein the compound of the Formula (I) is selected from the group consisting of compounds represented by the Formula (II):

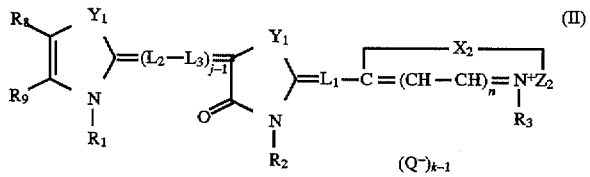

wherein $Z_2$ represents an atomic group necessary to form a saturated or unsaturated 5- or 6-membered ring selected from the group consisting of a thiazole ring, a benzothiazole ring, a naphthothiazole ring, an oxazole ring, a benzoxazole ring, a naphthoxazole ring, a selenazole ring, a benzoselenazole ring, a thiazoline ring, a 2-pyridine ring, a 4-pyridine ring, a 2-quinoline ring, a 4-quinoline ring, a 1-isoquinoline ring, a 3,3-dialkylindolenine ring, an imidazole ring, a benzimidazole ring and a naphthimidazole ring;

$Y_1$ represents O, S, Se, or

$X_1$ and $X_2$, which may be the same or different, each represents O, S, Se,

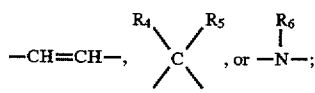

$R_1$ and $R_3$, which may be the same or different, each represents an alkyl group;

$R_2$ represents an alkyl group, an aryl group or a heterocyclic group;

$L_1$, $L_2$ and $L_3$, which may be the same or different, each represents a methine group or a nitrogen atom and $L_1$ and $R_3$ may combine and form a 5- or 6-membered ring;

Q represents a pharmaceutically acceptable anion;

j and k, which may be the same or different, each represents 1 or 2;

n represents 0 or 1;

$R_8$ and $R_9$, which may be the same or different, each represents a hydrogen atom, an alkyl group or an aryl group, or $R_8$ or $R_9$ may combine and form a fused 5- or 6-membered ring.

4. The composition of claim 1, wherein the compound of the Formula (I) is selected from the group consisting of compounds represented by the Formula (III):

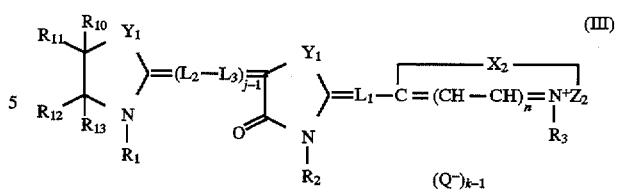

wherein $X_1$ and $X_2$, which may be the same or different, each represents O, S, Se,

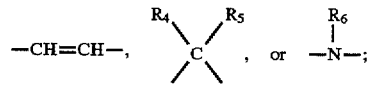

$Y_1$ represents O, S, Se, or

$Z_2$ represents an atomic group necessary to form a saturated or unsaturated 5- or 6-membered ring selected from the group consisting of a thiazole ring, a benzothiazole ring, a naphthothiazole ring, an oxazole ring, a benzoxazole ring, a naphthoxazole ring, a selenazole ring, a benzoselenazole ring, a thiazoline ring, a 2-pyridine ring, a 4-pyridine ring, a 2-quinoline ring, a 4-quinoline ring, a 1-isoquinoline ring, a 3,3-dialkylindolenine ring, an imidazole ring, a benzimidazole ring and a naphthimidazole ring;

$R_1$ and $R_3$, which may be the same or different, each represents an alkyl group;

$R_2$ represents an alkyl group, an aryl group or a heterocyclic group;

Q represents a pharmaceutically acceptable anion;

j and k, which may be the same or different, each represents 1 or 2;

$L_1$, $L_2$ and $L_3$, which may be the same or different, each represents a methine group or a nitrogen atom and $L_1$ and $R_3$ may combine and form a 5- or 6-membered ring;

n represents 0 or 1;

$R_{10}$, $R_{11}$, $R_{12}$ and $R_{13}$, which may be the same or different, each represents a hydrogen atom, an alkyl group or an aryl group, or any two of $R_{10}$ to $R_{13}$ may combine and form a 5- or 6-membered ring.

5. The composition of claim 1, wherein $R_1$ and $R_3$ each represents an alkyl group having from 1 to 15 carbon atoms; $R_2$ represents an alkyl group having from 1 to 15 carbon atoms, an aryl group having from 6 to 20 carbon atoms, or a heterocyclic group selected from the group consisting of an imidazole ring, a thiazole ring, a pyrrole ring, a pyrazole ring, a furan ring, a thiophene ring, a piperidine ring, a morpholine ring, a piperadine ring, a pyrazine ring, a pyridine ring, and a pyrimidine ring; $R_4$ and $R_5$ each represents an alkyl group having from 1 to 15 carbon atoms; $R_6$ and $R_7$ each represents an alkyl group having from 1 to 15 carbon atoms or an aryl group having from 6 to 20 carbon atoms.

6. The composition of claim 1, wherein $Y_1$ represents S and $L_2$ and $L_3$ each represents a methine group and Q represents chloride, bromide, iodide, p-toluenesufonate or acetate.

7. The composition of claim 1, wherein said cyclodextrin is selected from the group consisting of β-cyclodextrin, γ-cyclodextrin, hydroxypropyl-β-cyclodextrin and dihydroxypropyl-β-cyclodextrin.

8. The composition of claim 7, wherein said cyclodextrin is γ-cyclodextrin or hydroxypropyl-β-cyclodextrin.

9. An anti-cancer composition for treating a cancer sensitive to a rhodacyanine compound represented by formula (II), wherein said anti-cancer composition comprises therapeutically effective amounts of (a) a rhodacyanine compound

(13) a cyclodextrin, and (c) a solvent carrier, and wherein said rhodacyanine compound (a) is selected from the group consisting of compounds represented by the following Formula (II), the cation moiety of which has a log P value of 5–11, said cyclodextrin (b) is selected from the group consisting of β-cyclodextrin, γ-cyclodextrin, hydroxypropyl-β-cyclodextrin and dihydroxy-propyl-β-cyclodextrin and said solvent carrier (c) is water:

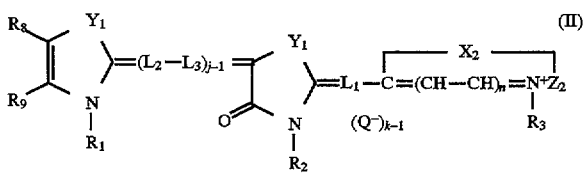

wherein $X_1$ and $X_2$, which may be the same or different, each represents O, S, Se,

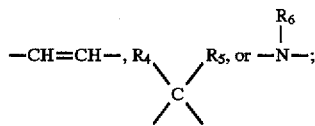

$Y_1$ represents O, S, Se, or

$R_1$ and $R_3$, which may be the same or different, each represents an alkyl group;

$R_2$ represents an alkyl group, an aryl group or a heterocyclic group;

$Z_2$ represents an atomic group necessary to form a saturated or unsaturated 5- or 6-membered ring selected from the group consisting of a thiazole ring, a benzothiazole ring, a naphthothiazole ring, an oxazole ring, a benzoxazole ring, a naphthoxazole ring, a selenazole ring, a benzoselenazole ring, a thiazoline ring, a 2-pyridine ring, a 4pyridine ring, a 2-quinoline ring, a 4-quinoline ring, a 1-isoquinoline ring, a 3,3-dialkylindolenine ring, an imidazole ring, a benzimidazole ring and a naphthimidazole ring;

$L_1$, $L_2$ and $L_3$, which may be the same or different, each represents a methine group or a nitrogen atom and $L_1$ and $R_3$ may combine and form a 5- or 6-membered ring;

$R_4$ and $R_5$, which may be the same or different, each represents an alkyl group;

$R_6$ and $R_7$, which may be the same or different, each represents an alkyl group or an aryl group;

$R_8$ and $R_9$, which may be the same or different, each represents a hydrogen atom, an alkyl group or an aryl group, or $R_8$ and $R_9$ may combine and form a fused 5- or 6-membered ring;

Q represents a pharmaceutically acceptable anion;

j and k, which may be the same or different, each represents 1 or 2; and n represents 0 or 1, wherein said amounts are effective to enhance the solubility of (a).

10. The composition of claim 9, wherein $R_1$ and $R_3$ each represents an alkyl group having from 1 to 15 carbon atoms; $R_2$ represents an alkyl group having from 1 to 15 carbon atoms; an aryl group having from 6 to 20 carbon atoms, or a heterocyclic group selected from the group consisting of an imidazole ring, a thiazole ring, a pyrrole ring, a pyrazole ring, a furan ring, a thiophene ring, a piperidine ring, a morpholine ring, a piperadine ring, a pyrazine ring, a pyridine ring and a pyrimidine ring; $R_4$ and $R_5$ each represents an alkyl group having from 1 to 15 carbon atoms; $R_6$ and $R_7$ each represents an alkyl group having from 1 to 15 carbon atoms or an aryl group having from 6 to 20 carbon atoms; $R_8$ and $R_9$ each represents a hydrogen atom, an alkyl group having from 1 to 15 carbon atoms or an aryl group having from 6 to 20 carbon atoms.

11. The composition of claim 9, wherein $Y_1$ represents S and $L_2$ and $L_3$ each represents a methine group and Q represents chloride, bromide, iodide, p-toluenesufonate or acetate, and said cyclodextrin is γ-cyclodextrin or hydroxypropyl-β-cyclodextrin.

12. The composition of claim 1, wherein said composition is an injectable composition.

13. The composition of claim 12, wherein the molar proportion of said rhodacyanine compound (a) to said cyclodextrin (b) is 1/10–1/500.

14. The composition of claim 12, wherein said rhodacyanine compound (a) is present in said injectable composition in amount of about 0.0001% to about 10% by weight based on the total weight of the composition.

15. The composition of claim 9, wherein said composition is an injectable composition.

16. The composition of claim 1, wherein the compound of the Formula (I) is selected from the group consisting of compounds represented by Formula (IV):

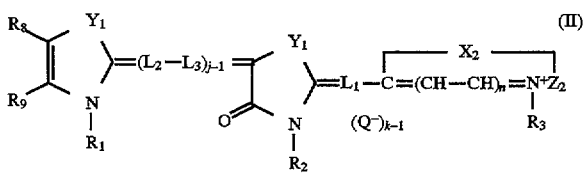

wherein $Y_1$ represents O,S,Se, or

$X_2$ represents O, S, Se,

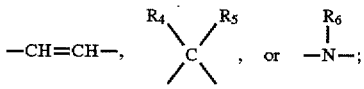

$Z_2$ represents an atomic group necessary to form a saturated or unsaturated 5- or 6-membered ring selected from the group consisting of a thiazole ring, a benzothiazole ring, a naphthothiazole ring, an oxazole ring, a benzoxazole ring, a naphthoxazole ring, a selenazole ring, a benzoselenazole ring, a thiazoline ring, a 2-pyridine ring, a 4-pyridine ring, a 2-quinoline ring, a 4-quinoline ring, a 1-isoquinoline ring, a 3,3-dialkylindolenine ring, an imidazole ring, a benzimidazole ring and a naphthimidazole ring;

$R_1$ and $R_3$, which may be the same or different, each represents an alkyl group;

$R_2$ represents an alkyl group, an aryl group or a heterocyclic group;

Q represents a pharmaceutically acceptable anion;

j and k, which may be the same or different, each represents 1 or 2;

$L_1$, $L_2$ and $L_3$, which may be the same or different, each represents a methine group or a nitrogen atom and $L_1$ and $R_3$ may combine and form a 5- or 6-membered ring;

n represents 0 or 1;

$R_{14}$, $R_{15}$, $R_{16}$, and $R_{17}$, which may be the same or different, each represents a hydrogen atom, an alkyl group, an aryl group, an alkoxy group, an aryloxy group, an acyl group, an alkoxycarbonyl group, a benzoyl group, an ureido group, an amino group, an amido group, a sulfamido group, a carbomoyl group, a sulfamoyl group, a halogen atom, a nitro group, a cyano group, a hydroxy group or a carboxyl group, or any adjacent two of $R_{14}$ to $R_{17}$ may combine and form a 5- or 6-membered ring.

17. The composition of claim 1, wherein the compound of the Formula (I) is selected from the group consisting of compounds represented by Formula (V):

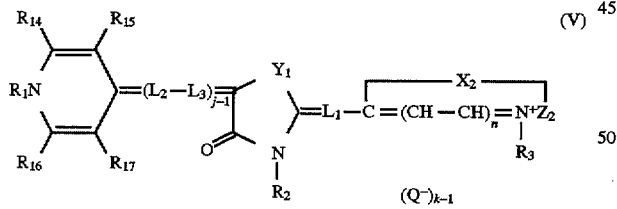

wherein $Y_1$ repsents O, S, Se, or

$X_2$ represents O, S, Se,

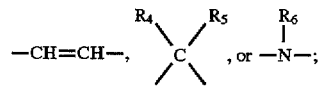

$Z_2$ represents an atomic group necessary to form a saturated or unsaturated 5- or 6-membered ring selected from the group consisting of a thiazole ring, a benzothiazole ring, a naphthothiazole ring, an oxazole ring, a benzoxazole ring, a naphthoxazole ring, a selenazole ring, a benzoselenazole ring, a thiazoline ring, a 2-pyridine ring, a 4-pyridine ring, a 2-quinoline ring, a 4-quinoline ring, a 1-isoquinoline ring, a 3,3-dialkylindolenine ring, an imidazole ring, a benzimidazole ring and a naphthimidazole ring;

$R_1$ and $R_3$, which may be the same or different, each represents an alkyl group;

$R_2$ represents an alkyl group, an aryl group or a heterocyclic group;

Q represents a pharmaceutically acceptable anion;

j and k, which may be the same or different, each represents 1 or 2;

$L_1$, $L_2$ and $L_3$, which may be the same or different, each represents a methine group or a nitrogen atom and $L_1$ and $R_3$ may combine and form a 5- or 6-membered ring;

n represents 0 or 1;

$R_{14}$, $R_{15}$, $R_{16}$ and $R_{17}$, which may be the same or different, each represents a hydrogen atom, an alkyl group, an aryl group, an alkoxy group, an aryloxy group, an acyl group, an alkoxycarbonyl group, a benzoyl group, an ureido group, an amino group, an amido group, an sulfamido group, a carbomoyl group, a sulfamoyl group, a halogen atom, a nitro group, a cyano group, a hydroxy group or a carboxyl group, or any adjacent two of $R_{14}$ to $R_{17}$ may combine and form a 5- or 6-membered ring.

18. The composition of claim 1 wherein said rhodacyanine compound is

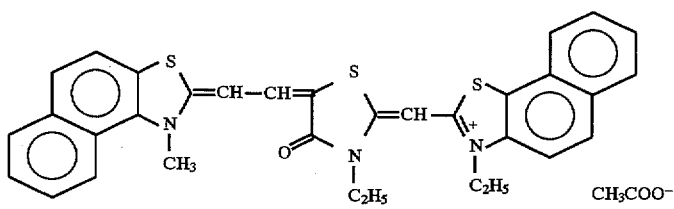

and said cyclodextrin is hydroxypropyl-β-cyclodextrin.

19. A method for treatment of cancer comprising administering, by injection, to a host afflicted with cancer, an anti-cancer composition for treating a cancer sensitive to a rhodacyanine compound represented by formula (I) below, wherein said anti-cancer composition comprises therapeutically effective amounts of (a) a rhodacyanine compound and (b) a cycledextrin, and wherein said rhodacyanine compound (a) is selected from the group consisting of compounds represented by the following Formula (I), the cation moiety of which has a log P value of 4.5–12:

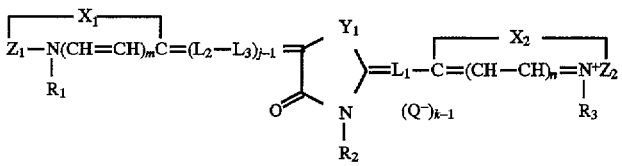

wherein $X_1$ and $X_2$, which may be the same or different, each represents O, S, Se,

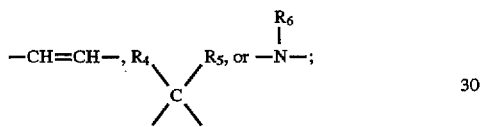

$Y_1$ represents O, S, Se, or

$R_1$ and $R_3$, which may be the same or different, each represents an alkyl group;

$R_2$ represents an alkyl group, an aryl group or a heterocyclic group;

$Z_1$ and $Z_2$, which may be the same or different, each represents an atomic group necessary to form a saturated or unsaturated 5- or 6-membered ring selected from the group consisting of a thiazole ring, a benzothiazole ring, a naphthothiazole ring, an oxazole ring, a benzoxazole ring, a naphthoxazole ring, a selenazole ring, a benzoselenazole ring, a thiazoline ring, a 2-pyridine ring, a 4-pyridine ring, a 2-quinoline ring, a 4-quinoline ring, a 1-isoquinoline ring, a 3,3-dialkylindolenine ring, an imidazole ring, a benzimidazole ring and a naphthimidazole ring;

$L_1$, $L_2$ and $L_3$ swhich may be the same or different, each represents a methine group or a nitrogen atom and $L_1$ and $R_3$ may combine and form a 5- or 6-membered ring;

$R_4$ and $R_5$, which may be the same or different, each represents an alkyl group;

$R_6$ and $R_7$, which may be the same or different, each represents an alkyl group or an aryl group;

Q represents a pharmaceutically acceptable anion;

j and k, which may be the same or different, each represents 1 or 2;

m and n, which may be the same or different, each represents 0 or 1, wherein said amounts are effective to enhance the solubility of (a).

* * * * *